(12) United States Patent
Dionne et al.

(10) Patent No.: US 7,702,481 B2
(45) Date of Patent: Apr. 20, 2010

(54) DIAGNOSTIC AND CONTROL SYSTEM FOR A PATIENT SUPPORT

(75) Inventors: Jean-Paul Dionne, Levis (CA); Nadine Trepanier, Charlesbourg (CA); Luc Landry, La Pocatiere (CA)

(73) Assignee: Stryker Canadian Management Inc., L'Islet, Quebec (CA)

( * ) Notice: Subject to any disclaimer, the term of this patent is extended or adjusted under 35 U.S.C. 154(b) by 826 days.

(21) Appl. No.: 11/362,365

(22) Filed: Feb. 23, 2006

(65) Prior Publication Data

US 2007/0164871 A1 Jul. 19, 2007

Related U.S. Application Data

(60) Provisional application No. 60/655,738, filed on Feb. 23, 2005.

(51) Int. Cl.
*G01C 9/00* (2006.01)
*G01C 17/38* (2006.01)
*G05D 1/10* (2006.01)

(52) U.S. Cl. .................... 702/150; 702/94; 700/302
(58) Field of Classification Search ......... 702/182–185, 702/94, 95, 150–154; 700/13, 17, 64, 302; 5/607–611, 616
See application file for complete search history.

(56) References Cited

U.S. PATENT DOCUMENTS

| 6,163,903 | A | 12/2000 | Weismiller et al. |
| 6,279,183 | B1 | 8/2001 | Kummer et al. |
| 6,353,950 | B1 | 3/2002 | Bartlett et al. |
| 6,651,279 | B1 * | 11/2003 | Muthuvelan ................... 5/600 |
| 6,876,303 | B2 * | 4/2005 | Reeder et al. ............. 340/573.1 |
| 6,897,780 | B2 * | 5/2005 | Ulrich et al. ............. 340/573.1 |
| 7,222,044 | B2 * | 5/2007 | Nakakita et al. ........... 702/147 |
| 7,472,439 | B2 * | 1/2009 | Lemire et al. .................. 5/607 |
| 2004/0172758 | A1 * | 9/2004 | Alakkat ......................... 5/610 |
| 2006/0136170 | A1 * | 6/2006 | Skinner ...................... 702/150 |
| 2006/0259267 | A1 * | 11/2006 | Narayanasamy ............ 702/150 |

FOREIGN PATENT DOCUMENTS

CA 2408342 11/2001

OTHER PUBLICATIONS

PCT Written Opinion of the ISA regarding PCT/CA06/000231, the international counterpart to the present application which currently contains the same claims as the present application.
PCT International Search Report regarding PCT/CA06/000231, the international counterpart to the present application.
PCT International Preliminary Report on Patentability regarding PCT/CA06/000231, the international counterpart to the present application.

* cited by examiner

*Primary Examiner*—Michael P Nghiem
(74) *Attorney, Agent, or Firm*—Van Dyke, Gardner, Linn & Burkhart, LLP

(57) ABSTRACT

The present invention provides a diagnostic and control system for a patient support, wherein the patient support includes one or more of a plurality of electronic elements. Such elements may include load sensors, tilt sensors, actuators for adjusting patient support angles, in addition to other electronic elements. The diagnostic and control system can enable the specific control of each of these electronic element for desired operation thereof and further can enable monitoring of the operating conditions of these electronic elements and additional patient support conditions.

11 Claims, 22 Drawing Sheets

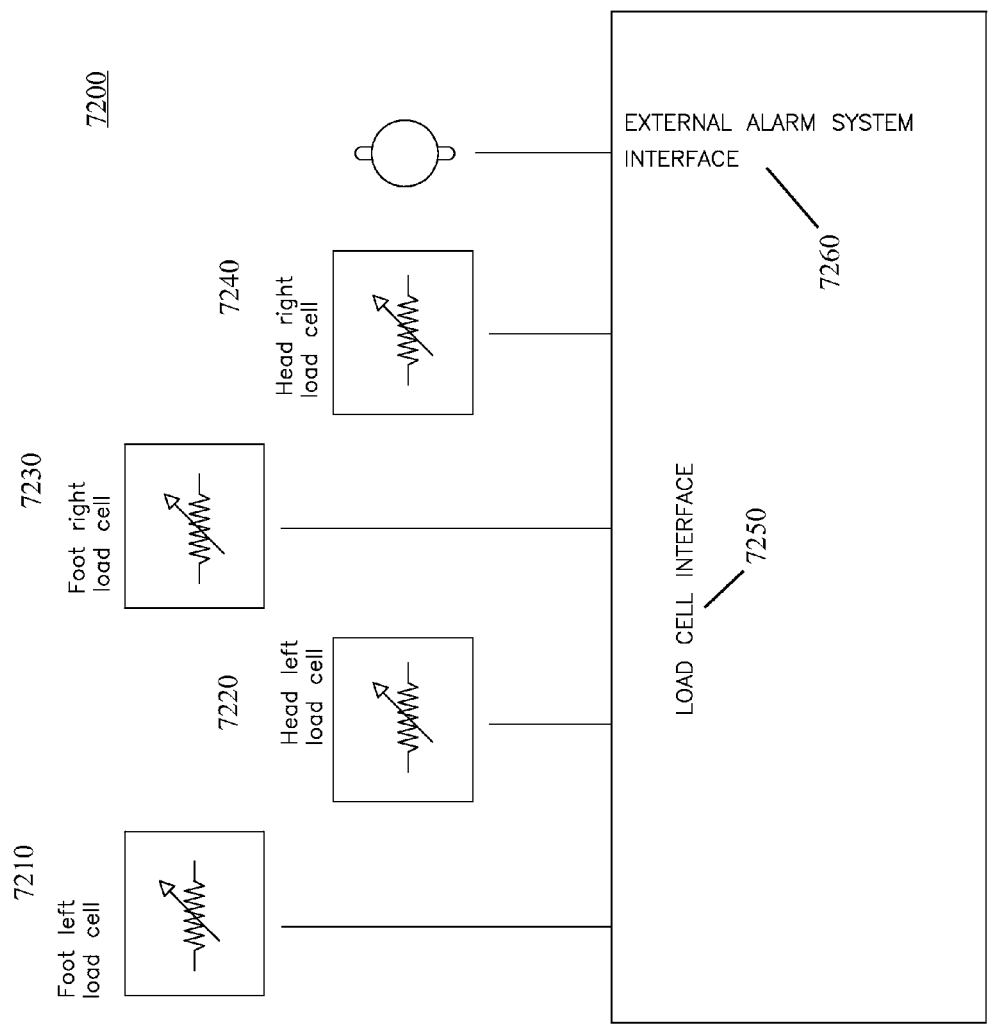

DIAGNOSTIC AND CONTROL SYSTEM FOR A PATIENT SUPPORT

CROSS REFERENCE TO RELATED APPLICATIONS

This application claims priority to U.S. provisional patent application Ser. No. 60/655,738 filed Feb. 23, 2005, the complete disclosure of which is hereby incorporated herein by reference.

FIELD OF THE INVENTION

The present invention pertains to hospital equipment systems and in particular to a hospital equipment system having a patient support status system for controlling and diagnosing the status of a hospital patient support.

BACKGROUND

Temporary and long term care of a patient generally requires that the patient be supported for the duration of the treatment. Currently available hospital beds are equipped with a number of complex mechanical and electrical subsystems which provide positioning, weight monitoring, and other functions related to patient's care. Despite their inherent complexity, these systems need to be easy to interact with and used by the caregiver. The ease of use and operation is of critical importance, particularly in emergency situations. Due to the complexity and required minimal downtime for these forms of beds, the status of such systems needs to be constantly monitored, which currently is performed by technicians in order to ensure desired functionality of the patient support is maintained. This form of monitoring and potentially diagnosis of problems with a patient support can be both time consuming and costly.

U.S. Pat. No. 6,897,780 to Ulrich, et al., entitled "Patient support Status Information System for Hospital Beds" discloses an information distribution system for a hospital, including a patient support having a signal generator for generating a first signal indicative of a condition of the patient support.

Therefore there is a need for a control and diagnostic system for integration into a multifunctional patient support that can overcome the identified problems in the prior art and provide the desired functionality with a reduced level of human intervention.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a diagnostic and control system for a patient support. In accordance with an aspect of the present invention, there is provided a diagnostic and control system for a patient support, said patient support having integrated therein one or more electronically controlled devices for providing one or more functions to the patient support, said system comprising: a control subsystem electronically coupled to one or more electronically controlled devices for transmission of data therebetween, said control system for controlling the functionality of the one or more electronically controlled devices, said control system collecting information relating to operational conditions representative of said one or more electronically controlled devices; and a diagnostic subsystem electronically coupled to the control subsystem for transmission of data therebetween, said control subsystem activating said diagnostic subsystem upon detection of an operational fault relating to the one or more electronically controlled devices, said diagnostic subsystem for receiving information from the control subsystem and analysing said information using one or more evaluation routines for the determination of a potential source of the operational fault.

Another object of the present invention is to provide a diagnostic and control system for a patient support, said patient support having integrated therein one or more electronically controlled devices for providing one or more functions to the patient support, said system comprising: a control subsystem electronically coupled to one or more electronically controlled devices for transmission of data therebetween, said control system for controlling the functionality of the one or more electronically controlled devices, a monitor subsystem electronically coupled to said one or more electronically controlled devices, said monitor subsystem collecting information relating to operational conditions representative of said one or more electronically controlled device; and a diagnostic subsystem electronically coupled to the control subsystem and monitor subsystem for transmission of data therebetween, said monitor subsystem activating said diagnostic subsystem upon detection of an operational fault relating to the one or more electronically controlled devices, said diagnostic subsystem receiving information from the monitor subsystem and analyzing said information using one or more evaluation routines for the determination of a potential source of the operational fault.

A further object of the present invention is to provide a diagnostic method for a patient support comprising a diagnostic and control system comprising the steps of: monitoring one or more electronically controlled devices of the patient support via a control subsystem, collecting information relating to operational conditions representative of one or more electronically controlled devices via said control subsystem, activating a diagnostic subsystem upon detection of an operational fault relating to the one or more electronically controlled devices, said diagnostic subsystem receiving information from said control subsystem, and said diagnostic subsystem analyzing said information using one or more evaluation routines for the determination of a potential source of the operational fault.

BRIEF DESCRIPTION OF THE FIGURES

FIG. 7C illustrates an embodiment comprising a scale or weigh subsystem.

DETAILED DESCRIPTION OF THE INVENTION

The present invention provides a diagnostic and control system for a patient support, wherein the patient support comprises one or more of a plurality of electronic elements including for example, load sensors, tilt sensors, linear sensors, temperature sensors, illumination sensors, humidity sensors, pressure sensors, electronic controls and keyboards, wiring actuators for adjusting patient support angles and the like, in addition to other electronic elements for example. The diagnostic and control system according to the present invention can enable the specific control of each of these electronic elements for desired operation thereof and further can enable the monitoring of the operating conditions of these electronic elements and additional patient support conditions. The diagnostic and control system further enables the evaluation and determination of the existence of one or more faults relating to the operation of the patient support, for example the existence of a fault can be conveyed to an operator in a form of an error message. The diagnostic and control system can subsequently evaluate the detected fault and can determine for example a cause thereof and a potential remedy. In this manner the diagnostic and control system according to the present invention can provide the evaluation of the detected fault and subsequently provide the operator or technician with a remedy for the detected fault, thereby reducing the downtime of a patient support that comprises the diagnostic and control system according to the present.

Patient Support

For example, multifunctional beds can have two or more different kinds of users. Persons who rest on the patient support namely supported persons who may have access to certain functionalities provided by the patient support and operators or personnel who can operate the same, more or other functionalities of the patient support either on-site or remotely. Operators may ensure that the patient support is adjusted to meet the requirements of a supported person who, for example, would otherwise not be able to adjust such functionality. For improved ergonomics, a patient support can have a multitude of adjustable characteristics such as providing individually reclinable sections or other functions to control or set the ambient conditions that a supported person may require for treatment. For example, the patient support may include an articulated surface to provide a supine position, as well as cardiac chair positions required for the treatment of cardiac patients.

Figure 1:
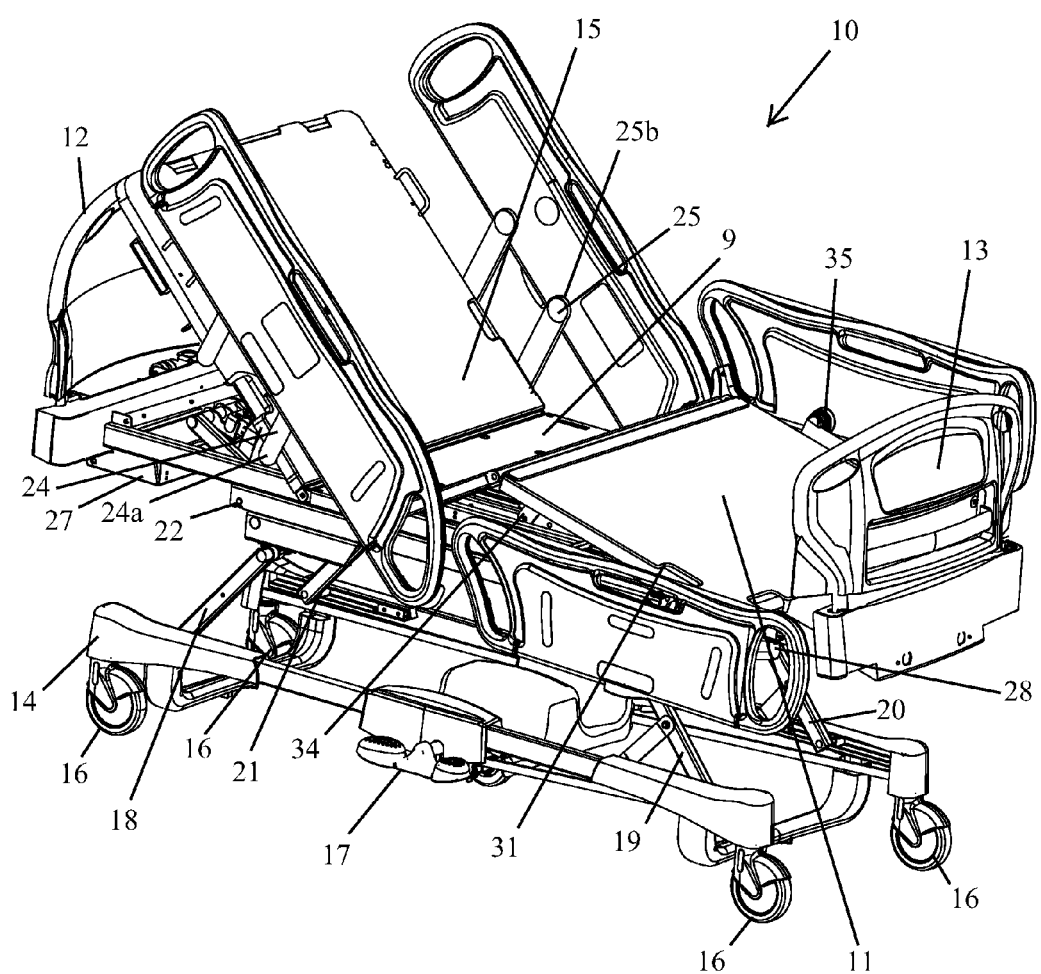
FIG. 1 illustrates an example of a hospital patient support into which the diagnostic and control system according to one embodiment of the present invention can be integrated.

An example of a hospital patient support into which can be integrated a diagnostic and control system according to an embodiment of the present invention, is illustrated in FIG. 1. The patient support 10 has an articulated patient support surface including a foot section 11, a seat section 9 and a head section 15 that are supported by a frame 22 and can also comprise a headboard 12 and a footboard 13. The frame 22 is supported on a base unit 14 by generally upright pivot plates 18, 19, 20 and 21 extending upwardly from the base unit 14. As illustrated, two pivot plates 18 and 21 are pivotally attached to the head portion 27 of the frame 22, and two pivot plates 19 and 20 are pivotally attached to the foot portion 28 of frame 22. Thus, the patient support can be raised or lowered when the pivot plates 18, 21, and 19, 20 rotate in order to provide vertical adjustment of the patient support 10 with respect to a horizontal plane. Preferably, the vertical adjustment of the patient support 10 can be further facilitated by a motor or a hydraulic lift (not shown).

If it is desired to render the patient support 10 easily movable, a plurality of wheels 16 can be provided on the base unit 14, typically at the four corners thereof. A brake/steer pedal 17 extends from the base unit 14 to facilitate locking and unlocking of the wheels 16.

A lift arm 24 is pivotally attached to frame 22 at a first pivot point 24a at one end and to the head section 15 at a second pivot point (not shown) at another end. Similarly, a lift arm 25 is also attached to the other side of the frame 22 at a first pivot point (not shown) at one end and to the head section 15 at a second pivot point 25b at the other end. The lift arms 24, 25 can be attached to the frame 22 and the head section 15 by a bolt or other fastening means that secures the lift arms 24, 25 to the frame 22 and the head section 15, while still allowing the lift arms 24, to pivot at the pivot points, such as pivot points 24a and 25b. Accordingly, transverse movement of the head section 15 toward and away from the foot section 11 will cause the respective lift arms 24, 25 to rotate together about the associated pivot points. In a similar manner, the foot section can be articulated with lift arms 34 and 35 which are pivotally attached at one end to frame 22 and at a distal end thereof to foot section 11, respectively, to provide for elevation of the foot section 11 with respect to the horizontal plane of the frame 22. As a result, the foot section 11 and the head section 15 can be configured and positioned at various degrees of inclination with respect to the seat section 9, which is fixed in the horizontal plane.

It would be readily understood that a variety of other patient support configuration can have the diagnostic and control system according to the present invention integrated therein and the specific example as described above is not to be considered limiting.

Patient support System Components

A multifunctional patient support can be equipped with one or more of a plurality of electronic devices that can provide a means for controlling the functionality of the patient support. For example, electronically controlled drivers or actuators can be provided to help automatically adjust any part or section of a patient support, wherein these actuators can be electrical, pneumatic or hydraulic in nature and may require a suitable electrical, pneumatic or hydraulic drive or power supply system for operation thereof. A patient support system can additionally include one or more sensors and detectors for sensing and detecting the status of structural or functional components of the patient support as well as certain vital signs of a supported person. For example, sensors or detectors can be appropriately designed load sensors, angular movement sensors, pressure sensors, temperature sensors or any other type of sensor or detector that would be appropriate for integration into a patient support as would be readily understood by a worker skilled in the art. Each of these sensors or detectors can be configured to evaluate a desired piece of information relating to the supported person or the patient support itself, for example the information can relate to the mass of the patient, the orientation of the patient support in terms of position of the supported person or other characteristics.

A communication system is provided to communicate with and control various functions of the patient support. In one aspect the communication system comprises one or more load cells and one or more tilt sensors for compensating weight measurements when the patient support is articulated. For example, one or more load cells to measure the weight on the patient support are located in positions where the load can be read.

One difficulty with determining the patient's weight occurs when the patient support is articulated or at positions other than the horizontally flat base position at which the load cells are usually calibrated. For example, when the lying surface support is angled in respect of the horizon or is articulated at various angles, the raw measurements on typical load cells will not reflect a patient's accurate weight since the load's center of gravity shifts, thereby affecting the individual load signals sensed by each load cell. An inclinometry method to determine the angular position of a patient by way of gravitational accelerometers. When an accelerometer is in a stationary position, the only force acting on it is the vertical gravitational force having a constant acceleration. Accordingly, the angular position of the patient can be calculated by measuring the deviation in the inclination angle between the inclination axis and the vertical gravitational force. Although the accelerometers can provide an effective way to measure the inclination in the patient's position, the resolution of the gravitational accelerometers is restricted to a limited range of inclination angles. The resolution of the angular position of a patient can however be improved by using dual axis (X-Y) accelerometers to sense the inclination angle with a higher degree of accuracy over a broader range of inclination. Advantageously, the gravitational accelerometers can be orientated in a variety of mounted angles, independent of any reference to other components of the patient support. As a result, a particular accelerometer can be positioned such that its effective resolution specifically targets the anticipated range of inclination for a given application.

To provide a more complete assessment of a patient's position, a plurality of gravitational accelerometers can be located in various parts of the patient support, for example connected to any parts of the lying surface that move. Output from the plurality of accelerometers can be compiled to provide a three-dimensional view of the patient's position. The angular inclination readings from the X-axis channel or the Y-axis channel of an accelerometer can be independently selected. Moreover, the sensed inclinations can be used to complement measurements from other sensors in the patient support, such as load cells. In one embodiment of the present invention, monolithic gravitational accelerometers are employed to further reduce the inaccuracies associated with mechanical sensors.

In addition, the patient support system comprises a form of human-machine interface system that can assist in accessing the functionalities that are associated with the patient support, for example to enable movement of portions of the patient support or to evaluate the condition of desired aspects of the patient support's functionality, such as monitoring or fault detection, for example. The interface system can be realised with one or more specific interfaces for enabling access, wherein interfaces can be provided on a footboard, headboard, side rails or other locations on the patient support for example. The position and number of interfaces can be determined based on the number of desired access points to the various functionalities of the components of the patient support.

In one embodiment, the patient support system components further comprises a sensor for detecting if a patient is inadvertently obstructing the selected movement of the patient support. For example, if a patient's limb is below a side rail, a sensor can detect the presence of the limb and not proceed with the lowering of the side rail if this request has been made. In this manner, the diagnostic and control system can monitor and evaluate if a patient's orientation or position would inhibit a selected movement of patient support component.

Control Subsystem

The diagnostic and control system can comprise a single monolithic subsystem or one or more modular subsystems enabling the control, monitoring, and, if required, calibration of the electronic components of the patient support system. In this manner the functionality of each of the electronic components, for example load sensors, temperature sensors, tilt sensors, actuator position sensors, actuators and the like can be evaluated and assessed for functionality within a desired set of parameters.

The diagnostic and control system can further monitor or query the functionality or status of the electronic elements, including for example, actuators, load sensors and the like. The system can monitor the current status of the operational parameters of these electronic elements and cross-reference the collected data with a set of standard operational characteristics. In this manner the system can be provided with a means for detection of a potential fault or error when a specific electronic element is not operating within a desired and/or predetermined range. For example, if a load sensor is being monitored and an extraneous load reading is detected, the system can re-query the load sensor to evaluate if it was merely an inaccurate reading or if a potential problem exists. This extraneous reading may be for example a reading that may be outside of normal operating conditions of the load sensor or may be evaluated as extraneous upon comparison with other load sensors in the vicinity, for example. Each of the electronic elements associated with the patient support system can be monitored in this manner as would be readily understood by a worker skilled in the art.

The diagnostic and control system can perform the monitoring of the patient support system components in a continuous manner, periodic manner or on-demand manner. The frequency of the monitoring of these components can be dependent on the electronic element being monitored. For example, the format of the monitoring can be dependent on the level of computation that is required to determine if a component is operating within desired and/or predetermined parameters. Constant monitoring may include querying the sensors for current readings for comparison with operational parameters. Periodic monitoring may be performed when evaluation of the orientation and angular position of the patient support frame is desired and on-demand monitoring may be performed on the diagnostic and control system itself wherein monitoring thereof would typically comprise a more extensive computation of current status.

In one embodiment of the present invention, the diagnostic and control system initialises or calibrates the operation of each of the electronic elements, for example actuators, load sensors and tilt sensors, in order that these electronic elements can provide the desired level of accuracy and desired functionality to the patient support. For example, calibration of a load sensor may be performed when a lying surface is positioned on the patient support and the load sensor can be zeroed under this condition. Furthermore, one or more of the actuators and tilt sensors can be calibrated or zeroed when a patient support is in a known orientation, for example linearly flat in a horizontal orientation.

In one embodiment of the present invention, the diagnostic and control system, while providing control of the functionality of the patient support system, can additionally ensure that a procedure requested by a user is both possible and safe to be performed. In this scenario the diagnostic and control system can evaluate the current status of the patient, support systems, and subsequently determine if the selected function is possible. For example if an operator requests the elevation of the head portion of the patient support, the system can determine if the head portion can be elevated, and if this procedure is possible, subsequently perform the desired function. If, for example, the head portion was fully raised, and the function was performed regardless, the actuator performing the requested function may be unnecessarily damaged due to overloading or over-extension, for example. This evaluation of the requested function can additionally be determined based on a current treatment being performed on a patient. For example, if a patient is to be oriented in a particular position, the diagnostic and control system can be configured to not allow any adjustment of the patient support system until this particular position can be changed according to treatment procedures or requirements.

In one embodiment of the present invention, the diagnostic and control system can be designed using an interface-controller-model architecture. The interface can provide user access to functions of the patient support, as well as a query or notification system that can provide access to patient support functionality, or notify monitoring personnel of important status information about parameters of patient support functionality in addition to certain vital information about the supported person. The model can provide an abstract description of the patient support's operational parameters, for example desired operating conditions in the form of a virtual machine, data set or database. The interface and controller can also read information from the model and based on current detected status of the electronic elements associated with the patient support, can determine if the patient support is performing within desired parameters. For example, a representational model for a collection of loads sensors can be provided which can provide operational parameters for the load sensors that can additionally be representative of the configuration of a load sensor web, thereby providing a means for evaluating the operational characteristics of the loads sensors during operation.

In one embodiment of the present invention, the diagnostic and control system can include one or more monitoring sensors that can provide a means for independently monitoring the functionality of one or more of the functions of the patient support. For example, a monitoring sensor can be associated with an actuator, wherein this monitoring sensor can be a temperature sensor that may enable the detection of overloading or overuse of an actuator due to an excessive temperature reading. The diagnostic and control system may optionally comprise redundant sensors for example, which may be activated upon detection of extraneous readings, for a typically used sensor. This form of redundancy can additionally provide a means for evaluating the operational characteristics of the electronic elements associated with the patient support.

In one embodiment, an interface associated with the diagnostic and control system can provide one or more different classes of functionalities to one or more different categories of users. For example functionalities can be categorized into functions accessible to a supported person, functions accessible to a monitoring person, and functions accessible to maintenance personnel for accessing diagnostic functionality. Consequently, there can be user interface subsystems that are available and intended for use by a specific user group. Functions of the patient support can also be grouped according to a person's physical accessibility to the patient support and can be accessible on-site or remotely or both. As a result, the patient support control system can interact with two or more physical tangible human-machine interface subsystems such as for example a console embedded in the patient support. Another important aspect of the present invention is the ability to connect to the patient support's control subsystem and diagnostic subsystem and transfer information therefrom or instructions thereto via a suitable number of user interface subsystems, for example communication systems using wired or wireless devices. Therefore, the diagnostic and control system according to one embodiment of the present invention provides the ability to obtain diagnostic information from the patient support via wireless devices or by connecting a computer or other wired communication device to the patient support. This provides an end user or a technician a means to access constructive information about the patient support for any repairs or maintenance that could be required. In a similar fashion, the monitoring personnel or health care provider can have access to information about the supported person without being in close proximity to the patient support incorporating the diagnosis and control system.

Upon the detection of a fault or error, the diagnostic and control system can activate an alarm setting that can be a visual, audible or other form of fault indication. For example, the interface associated with the patient support can have an error message displayed thereon. In one embodiment, this error message can provide a means for a technician to evaluate and correct the identified fault.

In one embodiment of the present invention, upon detection of a system fault during the monitoring of the functionality of the patient support system, the diagnostic and control system can initiate a full diagnostic subsystem which can perform a more complete system diagnostic evaluation and, in turn evaluate and identify one or more sources of the detected system fault.

In one embodiment of the present invention, the diagnostic and control system can collect specific information relating to the current status of particular components of the patient support system that are directly related to the detected fault, for example one or more sensor readings or the like, for subsequent use by the diagnostic subsystem for analysis of this fault.

Diagnostic Subsystem

The diagnostic and control system of the present invention comprises a diagnostic subsystem that can collect and evaluate the collected information relating to an identified fault and perform an analysis thereof in order to determine a source of such fault and a potential remedy to the detected fault. The diagnostic subsystem can indicate malfunctions of the patient support control system which can be due to a number of reasons such as for example an actuator break-down, an unacceptable deviation between a parameter of the patient support and the patient support control system's parameter's desired value as, for example, caused by overload or lack of calibration of an actuator, or any other condition of the patient support control system. A diagnostic program may be applied in order to make a distinction between any critical or non-critical function of the patient support control system when diagnosing a malfunction.

In one embodiment the diagnostic subsystem can also record a number of events including system data and user commands into one or more log records, for example one or more files in an embedded or a remote controller or computer system. Furthermore, essential information regarding any form of treatment administered to the supported person can be securely recorded which could be used in the future. The log records can also contain information from other subsystems of the patient support. Information in the tog records can be categorized; time stamped, and can contain human or machine-readable data describing the event. The data can be encoded, encrypted or clear text messages. Each subsystem can have its own logging mechanism for logging events specific to that subsystem, accessible only through an interface of the subsystem or accessible through interaction with a central controller. Events can be categorized into groups according to a severity or other schemes and, depending on the categorisation, include varying degrees of detailed information relevant to a particular category.

Figure 5:
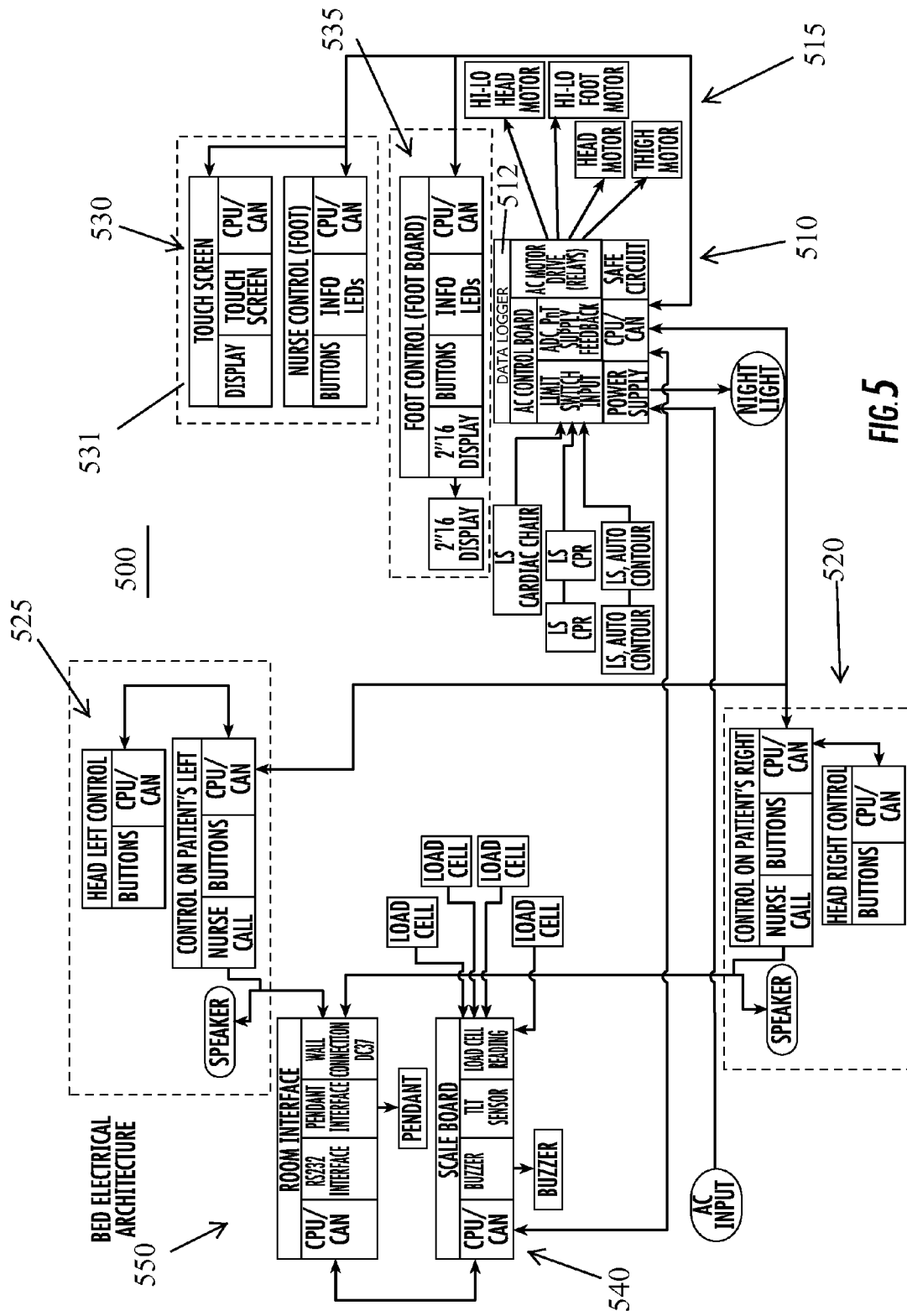
FIG. 5 schematically illustrates the electrical architecture of a diagnostic and control system according to one embodiment of the present invention.

In one embodiment of the present invention, the diagnostic and control system has a movement counting device (data logger) 512 which is used to produce a diagnostic that can be used to improve the design of the system for specific uses or to perform preventive maintenance on the system (FIG. 5). For example, it will be possible for an establishment utilising such a diagnostic and control system to use the data logger in order to determine the different ways in which the patient support is being manipulated and therefore provide information in a very constructive manner for any future designs. The information gathered by the data logger could also used in preventive maintenance such that more attention is given to any parts of the patient support that is involved in more motion or manipulation.

In one embodiment the diagnostic subsystem can analyse the detected information relating to the functionality of the patient support associated with the detected fault, and subsequently evaluate one or more indicators that can be compared with known indicators of known problems relating to patient support functionality. In this manner, based on a comparison with the indicators of known problems, the diagnostic subsystem can determine the specific problem. Once a specific problem has been identified, a possible corresponding remedy for this problem can be identified, thereby providing a means for the remediation of the identified problem. The correlation between a calculated indicator defined by information relating to the present status of the patient support system may not precisely match an indicator of a known problem. In this instance a probability of correlation between the evaluated indicator and the known indicator can be determined thereby providing a means for assigning a confidence factor with the identified problem.

In one embodiment of the present invention, the diagnostic subsystem can evaluate the identified fault through the analysis of previously detected readings, thereby providing for a correlation between the current readings at fault detection and previous readings. This manner of analysis may provide a means for identifying a malfunctioning component, for example a sensor through the correlation with previously detected values.

In one embodiment of the present invention, the diagnostic subsystem can be directly integrated into the patient support. Optionally, the diagnostic subsystem can be electronically coupled to the patient support upon the issuance of an error notification. Moreover, the patient support system architecture can comprise a diagnostic interface providing access to the patient support system such that a diagnostic subsystem can be separated or detached from the physical patient support and provide the same set, a subset or superset of diagnostic tools than an integrated diagnostic subsystem.

In one embodiment of the present invention, the diagnostic and control system comprises a communication system that can provide a means for transmitting information relating to the evaluated functionality of the patient support to another location. In this embodiment, the communication system can enable wired or wireless communication. For example, this form of connectivity of the patient support may enable the remote monitoring of patient support functionality at a location removed from the location of the patient support. For example, in a hospital setting, this remote monitoring can be performed at a nursing station or optionally can be provided at a remote location removed from the hospital. The communication system can enable the transmission of monitoring and diagnostic results to a technician for analysis, for example if a more detailed diagnostic analysis of the patient support is required in order to determine the source of the indicated error. This can provide a means for a detailed diagnostic to be performed and an appropriate remedy identified prior to the dispatching of a technician to the patient support site. In this manner, time may be saved as the technician may be dispatched with appropriate replacement parts, thereby reducing the downtime of the patient support.

The functionality of the diagnostic and control system according to the present invention can be provided by any number of computing devices, for example one or more microprocessors, one or more controllers or one or more computer systems that can be integrated into the patient support itself in order to provide the desired computational functionality. In one embodiment of the present invention, the diagnostic subsystem can be configured for coupling to the patient support to subsequently provide the diagnostic capabilities. It would be readily understood how to couple the diagnostic and control system to the one or more electronic elements in order to data transfer therebetween, for example this connection can be a wired or wireless connection.

FIG. 1 illustrates an example hospital patient support having components that can be controlled, monitored and diagnosed by one embodiment of the diagnostic and control system according to the present invention. The patient support is shown with some of its sections placed in one possible configuration. This example of a patient support is not to be considered limiting as the diagnostic and control system according to the present invention can be integrated into any number of patient support configurations.

Figure 2:
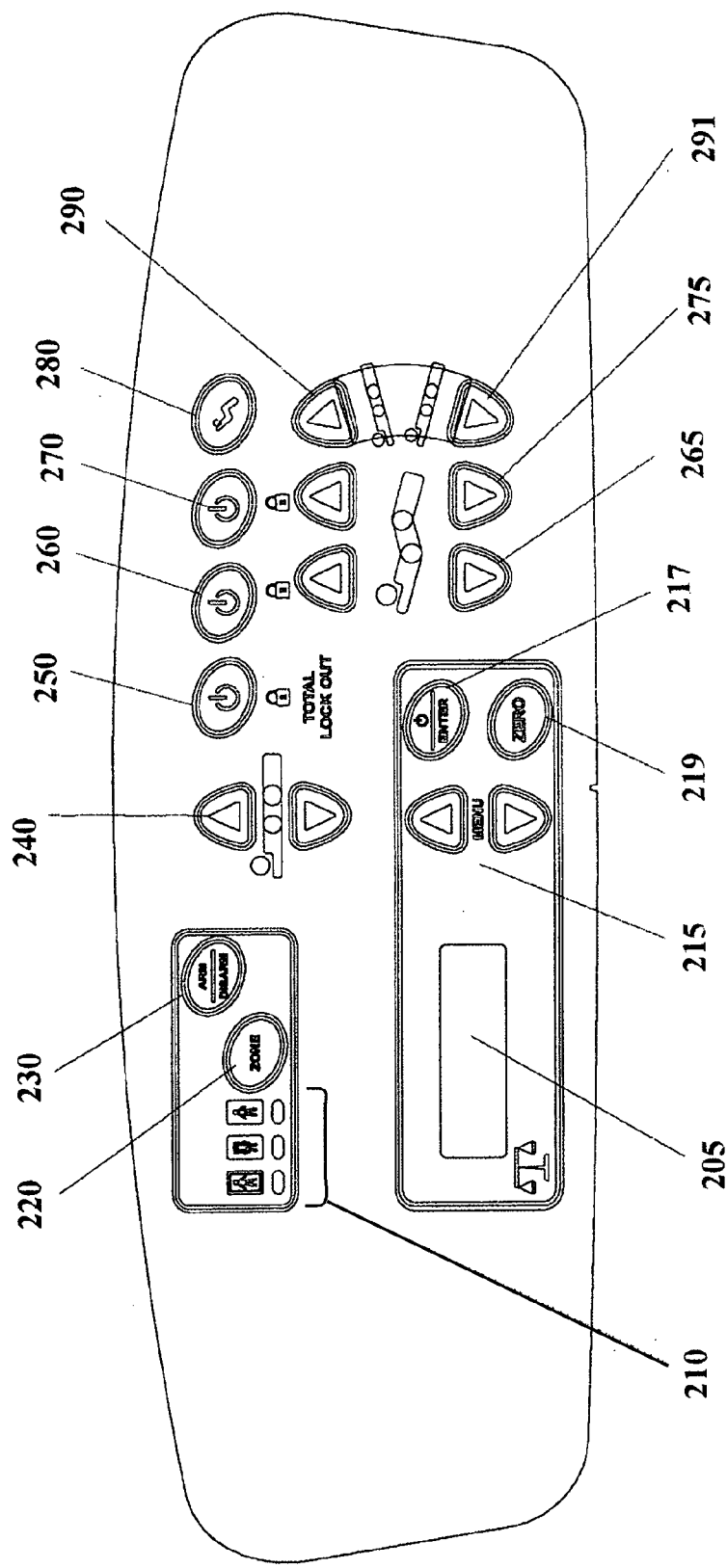
FIG. 2 illustrates a part of a user interface according to one embodiment of the present invention embedded into the patient support illustrated in FIG. 1.

FIG. 2 illustrates a schematic view of one embodiment of a console or interface that can provide access to some or all functionality of the diagnostic and control system, wherein this user interface may be embedded into a patient support. The console can be integrated into the foot board of the patient support illustrated in FIG. 1 and can provide access to the patient support's functions. The console has back lit zone indicators 210 which can indicate a set zone mode of the patient support for indicating a preset restriction level for movement of a supported person. Indicators 210 can also be multi-color back lit to indicate an armed or disarmed state. Button 220 can be used to set and switch between the zone alarms as indicated by the zone alarm indicators 210. Button 230 can arm or disarm the zone alarm functionality in a toggling fashion. Button 230 can be sectional or full color or multi-color back lit to indicate an armed or disarmed state of the zone alarm system. Interface elements 240 can be used to raise or lower the patient support surface. While pushing the arrow-up button the patient support raises and while pushing the arrow-down button the patient support lowers. Pushing and holding both buttons may cause the movement to stop or continue the movement according to the button which was pressed first.

Button 250 can lock out some or all functionality accessible through this or other consoles until the button 250 is pressed again. Buttons 260 and 270 can be used to lock-out access to reorient the respective head and knee sections of the patient support. Button 280 when pressed causes the patient support to assume a cardiac position or other predetermined shape of the patient support surface. Each of buttons 290 and 291 when pressed individually inclines or reclines the overall patient support surface without affecting the shape of the patient support surface. Interface elements 265 and 275 provide button groups which when pressed can reorient the head or the knee sections of the patient support and can be used in order to achieve respective desired angles between the upper body and the upper leg, as well as the upper leg and the lower leg of a supported person. Display 205 can be used to display information about certain functions or the state of certain parts of the patient support and its system components. Button group 215 can be used to scroll through information which is available in form of a menu for display but exceeds the amount of information which can be displayed simultaneously on display 205. Buttons 217 and 219 can be used to select or enter information and to interact with the menu following a command and control concept.

Figure 3:
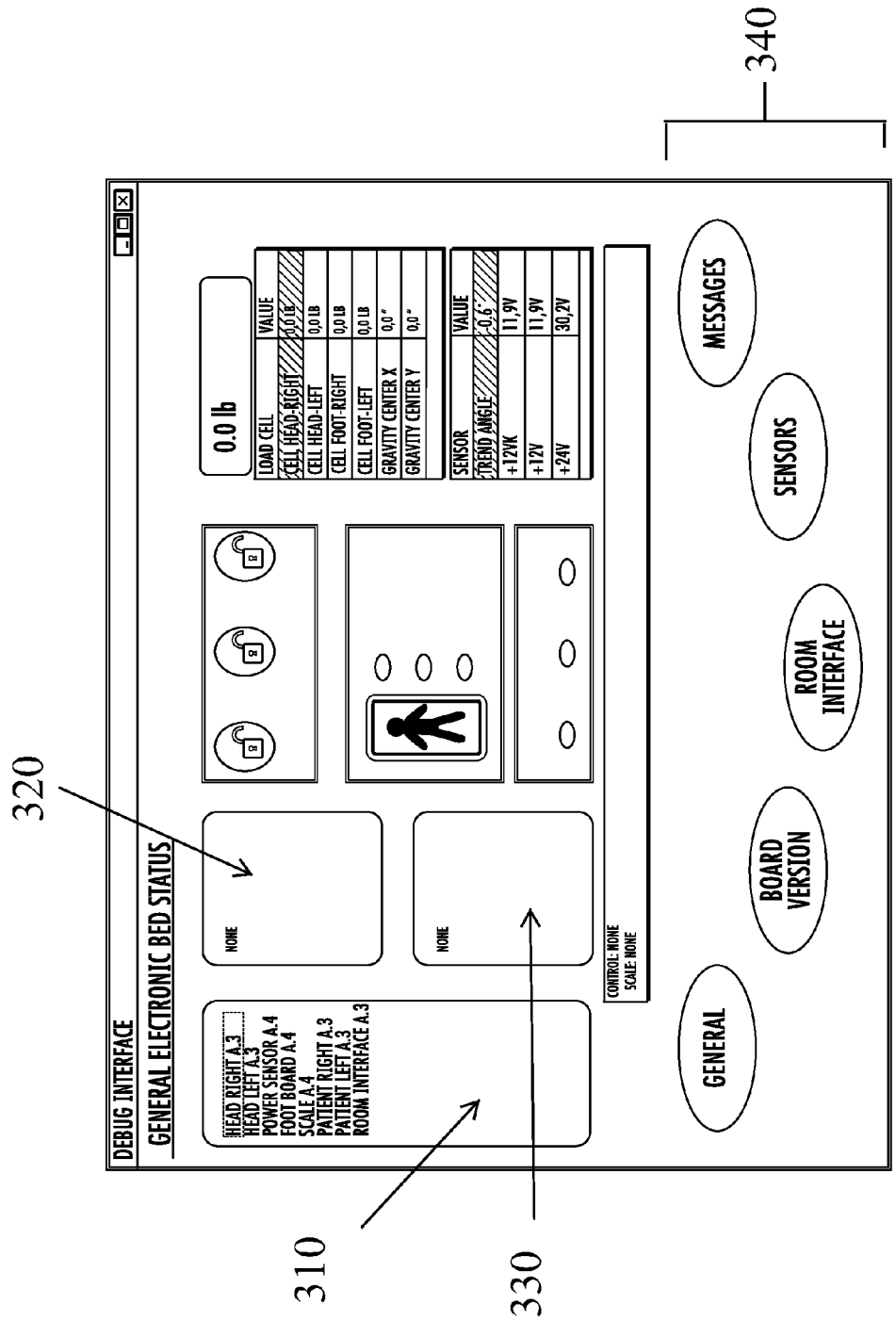
FIG. 3 illustrates the window content of a step in a series of user-patient support interaction processes displayed on a detached device such as a general purpose computer according to one embodiment of the present invention.

FIG. 3 illustrates an embodiment of the window content of a step in a series of user patient support interaction processes that can be displayed on a detached device such as a general purpose computer. This is part of an interface that for example can provide remote access to control, diagnose, or monitor functions of the patient support system. The interface can provide functions to select certain components from a list of components or subsystems 310 of the patient support system for detailed investigation. The user interface may change its look and feel by changing some or all of its user interface components when selecting to investigate a specific component of the patient support system. The user interface can provide and display information in a categorized graphical fashion and can utilize a button status field 320, a motor status field 330, fields for monitoring vital information about a supported person etc. The user interface can also provide a menu system 340 to select from and to provide access to different aspects of interaction of the patient support system such as for example, a monitoring interface, a maintenance interface, an operator interface etc. For example, a maintenance interface or menu can be presented to an end user or a technician. The maintenance menu is able to convey very accurate information in regards to any faulty components in the patient support so that the end user or technician can undertake appropriate action. The maintenance menu can be transferred to a computer, a server or other external device allowing the information to be displayed to the end user or technician via a computer or terminal. Therefore, remote diagnostic of the patient support can be achieved thus improving efficiency in remedying the fault. Switching between monitoring interface, maintenance interface, operator interface etc. may require authorization and may be password or security code protected.

Figure 4:
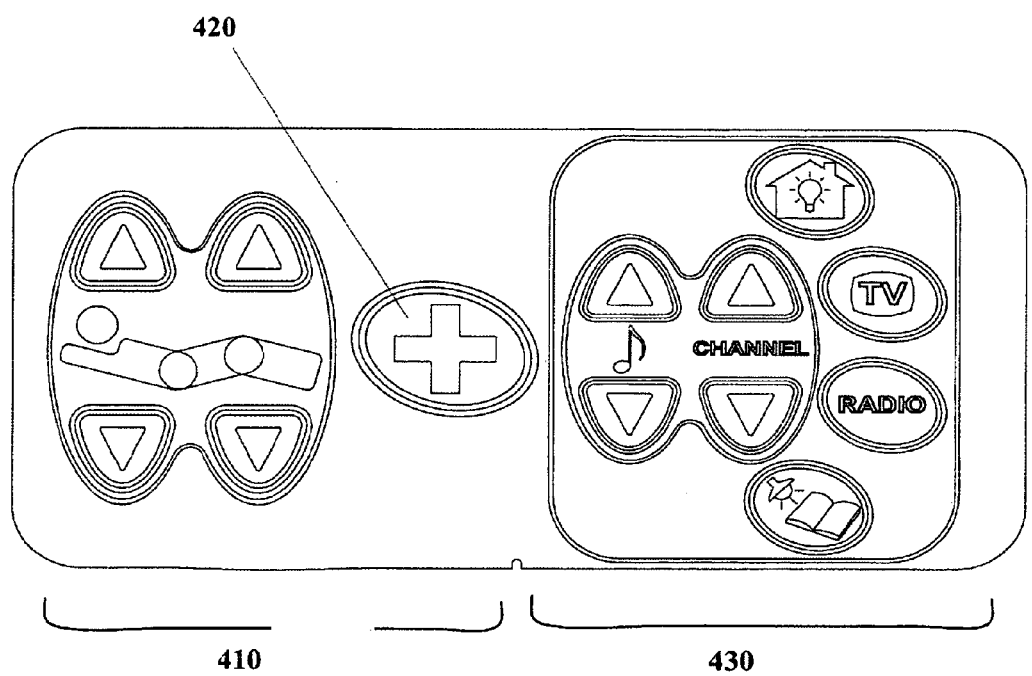
FIG. 4 illustrates an embodiment of a part of a user interface intended for use by the supported person according to one embodiment of the present invention.

FIG. 4 illustrates a part of the user interface intended for use by the supported person, according to an embodiment of the present invention. As illustrated, the user interface for the supported person can provide access to reclining functions 410, emergency call functions 420 or control of entertainment equipment 430.

FIG. 5 illustrates a schematic diagram of the system architecture 500 of a patient support control and diagnostic system. The architecture can be divided into a number of user interface and control subsystem components. The system architecture comprises a power or AC control system 510 for supplying electrical power, an actuator subsystem 515 providing ability for positioning and orienting parts of the patient support, a number of sensor and detector subsystems for sensing and detecting the state of parts of the patient support, and a diagnostic subsystem as indicated. The diagnostic subsystem can interact with the sensor and detector subsystem or it can have its own redundant sensor and detector system. The user interface subsystem can comprise a number of control consoles 520, 525, 530, and 535 comprising indication or display systems. The display systems can have a touch screen 531 or a regular display with separate buttons. The sensor system can comprise a scale subsystem 540 including a load cell system. The system architecture can further comprise a room or other interface 550 for communicating information to and from the patient support and a remote user interface system.

In one embodiment the patient support system architecture further comprises a model subsystem or virtual state machine for representation of the state of the patient support components for interaction with the controller and the user interface under operating conditions. Each control subsystem can comprise its own model and independent processor or the model of the subsystem can be integrated in a central program controlled by a central processing unit controlling the patient support system.

In one embodiment the architecture may include a diagnostic subsystem for monitoring or querying the functionality or status of the patient support components. The diagnostic subsystem can be separate from or simply an additional component of the one or more control subsystems. The diagnostic subsystem can monitor some or all of the patient support actuators and can utilize an operatively required and already present sensor system or the diagnostic subsystem can have its own redundant sensor system for improved reliability of the patient support control system. The diagnostic system may monitor the patient support components on a continuous, basis during the patient support's normal or intended operation or it may be activated only when required to perform certain maintenance procedures. None, some or all of the functions intended for use during normal operation of the patient support may be available during some or all of the diagnostic maintenance procedures. In addition, it may be safe for a person to remain in the patient support during none, some or all of the diagnostic maintenance procedures.

In one embodiment the diagnostic subsystem can comprise sensors for the purpose of self diagnosis of the patient support control system sensing the status of actuating components for example. Such sensors may not be required to sense the status of the patient support per se but rather provide access to important status' information of the control system. Examples can include the temperature of actuator components or controller hardware.

In one embodiment of the present invention, the diagnostic subsystem can passively alert users through messaging systems, for example error messages displayed on the display system. The diagnostic subsystem may also provide procedures to actively query internal status information of the patient support system not intended for use during normal operation. Examples of internal status information can include any kind of readings from sensors or results from self-diagnostic modes of employed digital devices. This information can be important, for example, when calibrating actuators and their respective motion sensor system to accurately scale sensor readings to provide positioning information that corresponds with the true physical position of the respective patient support component. Other examples for internal status information include power supply voltages or current readings.

In one embodiment the diagnostic subsystem can also include a debug mode permitting the step-by-step execution of commands or procedures of the microcontroller or processing unit. For example, the diagnostic subsystem could be accessed via a general purpose computer for extensive debugging of such subsystem.

The communication between different components within the patient support control and diagnostic system is achieved through network" communication between components such as CAN-Open for example. This protocol utilizes the broadcast of information to the different electronic components (or module) within the patient support. Information regarding any commands requested by the end user is thus transferred to every single electronic component within the patient support and thereafter, action is taken by the component (or module) which is concerned by the information that has just been broadcast. Alternatively, the communication between different components within the patient support control and diagnostic system can be achieved by a peer-to-peer network communication system or any other network communication protocol that would be known to a worker skilled in the art.

Figure 6:
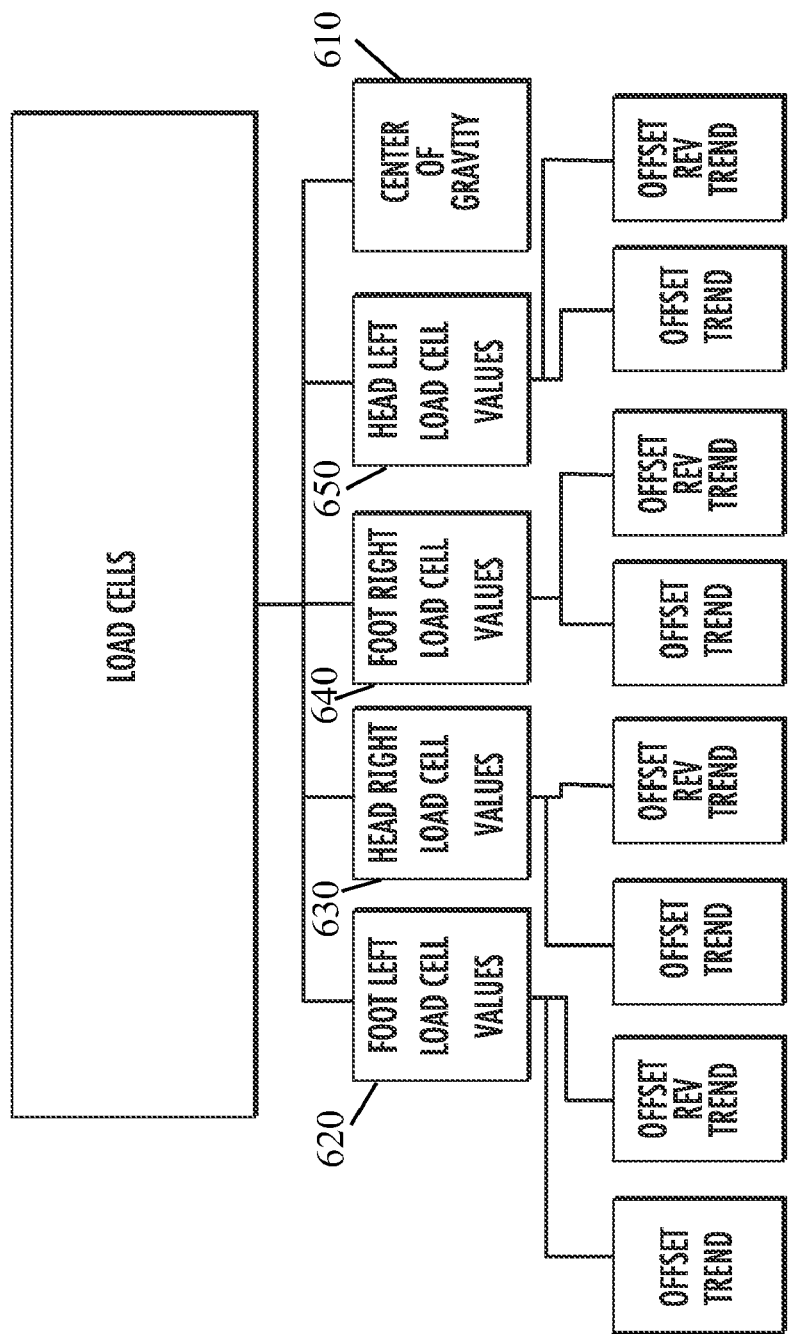
FIG. 6 illustrates an embodiment of a load cell system that can be used for monitoring movement, evaluating mass or weight of a supported person.

FIG. 6 illustrates an embodiment of a load cell system 600 that is used for monitoring movement of a supported person. The system can be integrated into the patient support or can be part of a person support element such as a mattress. In addition, the load cell system can comprise a number of load cells or load sensors for example a load cell which can be embedded in the patient support proximally positioned at each of a supported person's limbs and optionally at the center of the patient support. The load cell system also can be comprised of a mesh of load cells for example. The signals from the load cells can be monitored and processed by a processing unit in the load cell system or a central processing unit capable of monitoring, processing, and controlling signals from the patient support's subsystems. Instead of forming part of a support element such as a lying surface the load cell system can also integrated into the surface of the patient support for supporting the support element. The load cell system can provide a measure for the pressure, weight, or mass load of a certain load cell, for example foot left 620 or right 640 load cell values and head left 650 or light 630 load cell values and additional information about the location of the center of gravity.

In one embodiment the diagnostic and control system can comprise an additional scale subsystem providing a calibration process for calibrating the, scale subsystem to provide accurate reading of a supported person's weight and subsequently to calibrate a motion detection system for monitoring movement of a supported person. It may be necessary to calibrate the load cell electronics in order to provide a match of the sensor signals with the scale subsystem electronics.

Figure 7A:
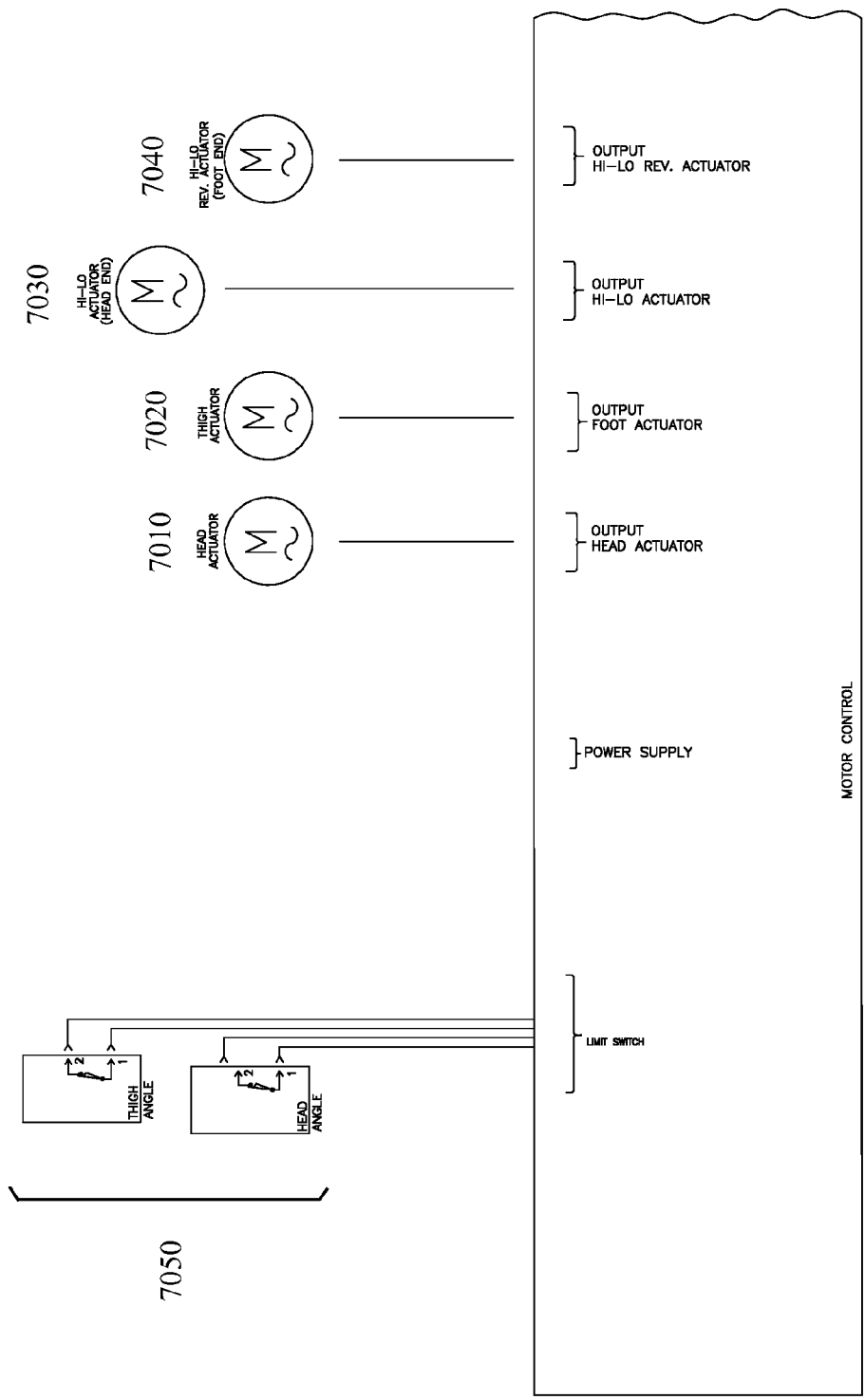
FIG. 7A illustrates an embodiment comprising a motor control, and motor and actuator system.

FIG. 7A schematically illustrates an embodiment of the motor control subsystem with a number of attached actuators and limit switches. It is understood that, depending on the functionality of the patient support, there can be different numbers of actuators or limit switches than illustrated. In this embodiment the surface of the patient support can be shaped by orienting a head, thigh, and a foot section where the support surface for a supported person is intended to fold and provide an adjustable angle between the upper body and the thigh as well as under the knee between the thigh and the lower leg. The head actuator 7010 can position the end of the head section, and the thigh actuator 7020 can position the knee section of the of the patient support surface relative to an even support structure. The HI-LO head actuator 7030 can position the head end of the even support structure relative to the frame of the patient support which is in contact with the floor. The HI-LO foot actuator 7040 can position the foot end of the even support structure relative to the frame of the patient support, for example. The two HI-LO actuators 7030 and 7040 can pivot the support surface horizontally whereas the head and the thigh actuator can shape the support surface by pivotally adjusting sections of the patient support surface.

In one embodiment, the motor control subsystem is connected to a number of limit switch or angle sensor systems 7050 which ensures that the actuators do not move or position parts beyond predetermined limit angles or distances. When a part or section of the patient support reaches a predetermined limit position while moving, the motor control subsystem can receive a status change signal via one or more limit sensor signals and can interrupt the respective movement. The motor control subsystem can have a safety control feature that does not allow any further continued movement in that same direction or orientation unless the limit condition indicated by the limit sensor system is resolved. Provided that no movement of other degrees of freedom of the patient support takes place the limit condition typically can be resolved by reversing the original movement.

As discussed previously, each component of the motor control system including the actuators and the limit switch sensor system can provide diagnostic features or a diagnostic mode. The diagnostic features also can include a separate redundant diagnosis sensor subsystem for monitoring the state of the respective device or component for example a temperature sensor or a redundant parallel or serial sensor limit switch system to enhance the reliability of the positioning system. An important aspect of the diagnostic subsystem that is relevant to the motor control system can regard the accurate calibration of sensors providing actuator position information. The motor control system interprets actuator position sensor signals to be accurate representations, encoded in form of a suitable signal, of the real position of a respective part or section of the patient support. The motor control system may fail to execute a given command when the real position deviates from the motor control system's perceived position as provided by or derived from an actuator signal. In such a case the diagnostic system can provide functionality to help avoid or diagnose a malfunction which can reach from functionalities such as automatic recalibration to alerting or messaging.

Figure 7B:
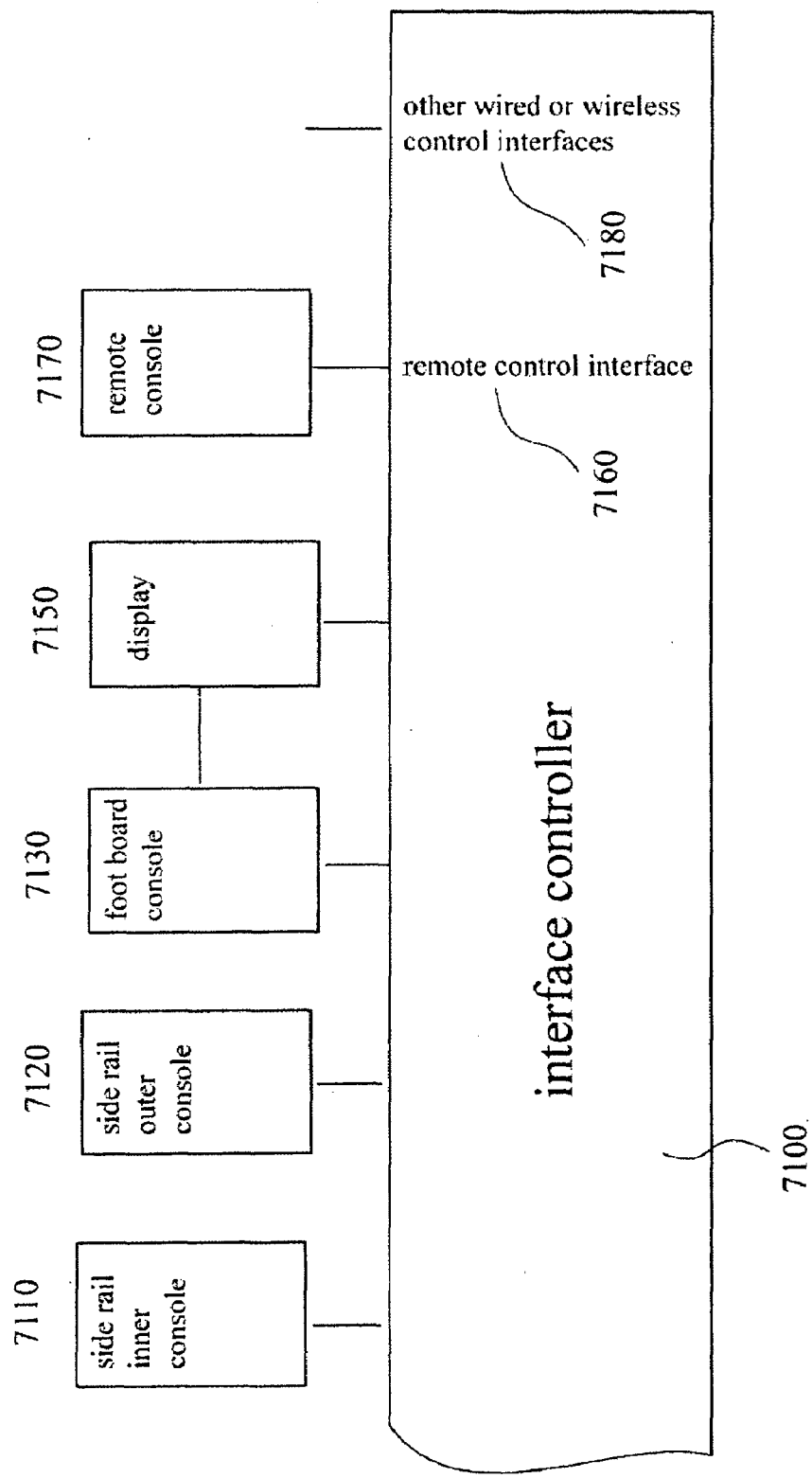
FIG. 7B illustrates an embodiment comprising an interface controller.

FIG. 7B schematically illustrates an embodiment of the user interface controller 7100 with a number of attached user interface consoles. The patient support can have a number of user-interface consoles each providing access to a certain set of patient support system functions. For example the patient support can have user interface consoles integrated into one or both of the side rails of the patient support providing easy access to certain patient support system functions to a supported person or a person at the side of the patient support. The patient support can also have a user interface console located at the foot or the head section of the patient support. Each such interface console may be integrated into a respective foot or head board of the patient support for example. A foot 7130 or a head interface console may provide access to a set of patient support system functions different from each other as well as different from the side rail consoles. There can be inner 7110 or outer 7120 side rail consoles intended for access from within or from outside of the patient support. An embodiment of a side rail interface console is illustrated in FIG. 4 and an embodiment of a foot board interface console is illustrated in FIG. 2. The foot board console can have a display system 7150 included. The display system can be a touch screen display or a simple passive display system with a separate input system as illustrated in FIG. 2. In addition the interface controller can have a remote control interface 7160 to which a remote console 7170 can be connected. The remote control interface 7160 can provide wired or wireless connection to a specialized or a general purpose computing device for example. A number of different bus systems and control protocols are available to communicate through the remote control interface as discussed previously and as would be known to a person skilled in the art. The interface controller may also provide a number of additional control or remote control interfaces 7180.

In one embodiment the interface controller as well as the attached user interface consoles can have self-diagnosis features or provide an interface for access to diagnostic procedures. The interface controller may be able to provide a debugging mode for step-by-step execution of control commands or to query status information of the components or devices of the patient support system.

FIG. 7C illustrates a part of a scale subsystem 7200 according to one embodiment of the present invention. The scale subsystem can connect to a number of load sensors. The number of load sensors can be different from the ones illustrated. In this embodiment four 20 load sensors 7210, 7220, 7230, 7240 which are capable of sensing pressure and can be calibrated to provide a measure of force or weight applied to each sensor are attached to the scale subsystem control interface 7250. The scale subsystem controller can process signals incoming from the load cells and can be used to detect the status of a supported person. The scale control subsystem can be configured to provide a messaging signal or to alert monitoring personnel through an external alarm system interface 7260 for example. If each load cell is properly calibrated, the scale control subsystem can also provide a measure of the weight of a supported person. The information can be utilized to determine a person's mass or weight or the respective mass or weight and can also be used to record this information in another subsystem of the patient support that may be desired for patient monitoring for example.

In one embodiment, the scale subsystem may require occasional calibration depending on the nature of the chosen sensor technology. Access to the scale subsystem for calibration, monitoring or diagnostic purposes may be possible through the user interface as described in FIG. 7B.

It is understood that any kind of diagnostic procedure also includes inspection of the corresponding component and that each component may provide a hardware interface for connection to a special purpose diagnostic device for diagnosing the component.

EXAMPLES

Example I

The Use of Loads Cells and Tilt Monitor Patients on a Patient Support

A patient support according to the present disclosure is shown in FIG. 1. The patient support with a head end and a foot end comprises a lying surface supported by a frame system. It also comprises a pair of head end siderails, a pair of foot end siderails, a headboard, a footboard, a power system and a communication system. The frame system comprises a lying surface support moveably connected to a load frame by an articulation system providing means for pivoting sections of the lying surface support relative to the load frame, a head end support arm pivotally attached to the head end of the load frame, a mobile frame translationally attached to foot end of the load frame, an intermediate frame being operationally connected to the load frame by a plurality of load cells and movably connected to a base frame by an elevation system, the elevation system providing a means for raising and lowering the intermediate frame relative to a base frame, the base frame being supported on the floor by a plurality of caster wheels, including a drive wheel operatively connected to assist in movement of the patient support.

Head end siderails are coupled to the head section of the lying surface support and may be moved between raised and lowered positions. Foot end siderails are coupled to the load frame and may also be moved between raised and lowered positions. The headboard is removably connected to the load frame and the footboard is connected to the mobile frame.

A communication system is provided to communicate with and control various functions of the patient support. Communication system and the remainder of patient support are powered by an AC source or a battery source (supported by the frame system).

Figure 10:
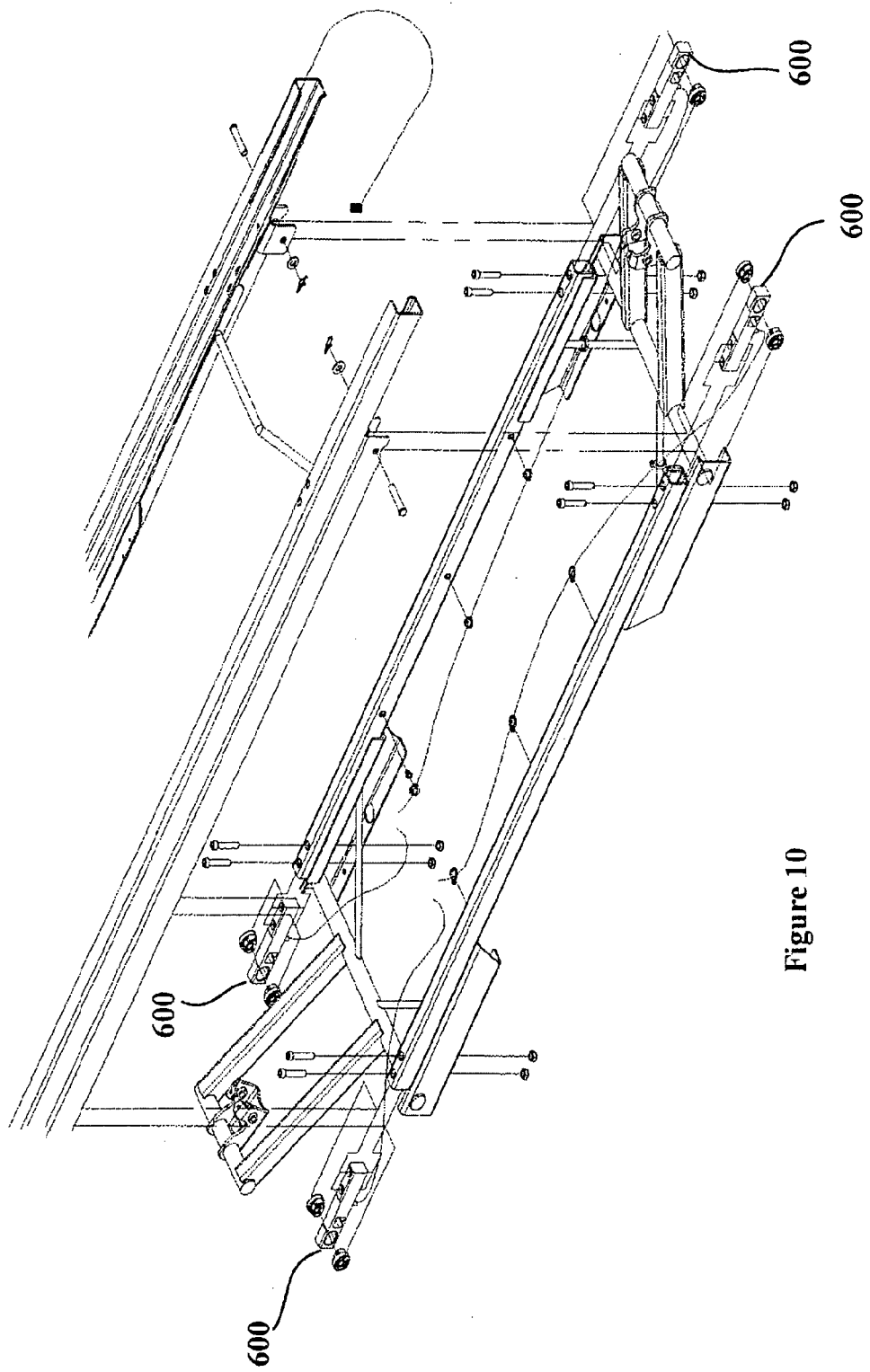
FIG. 10 is a partial exploded perspective view of an articulation mechanism according to one embodiment of the present invention in relation to a load frame and an intermediate frame.

As described above and referring to FIGS. 10, 11, and 12, load cells 600 can be positioned at one or more locations in the frame system of the patient support such that measurements of various load signals can be achieved. Load cells 600 generate load signals indicative of forces applied to the load cells 600.

Accurate load cell readings are important for various reasons such as determining the weight fluctuations of a patient over time and the patient's center of gravity at any given time.

Figure 11:
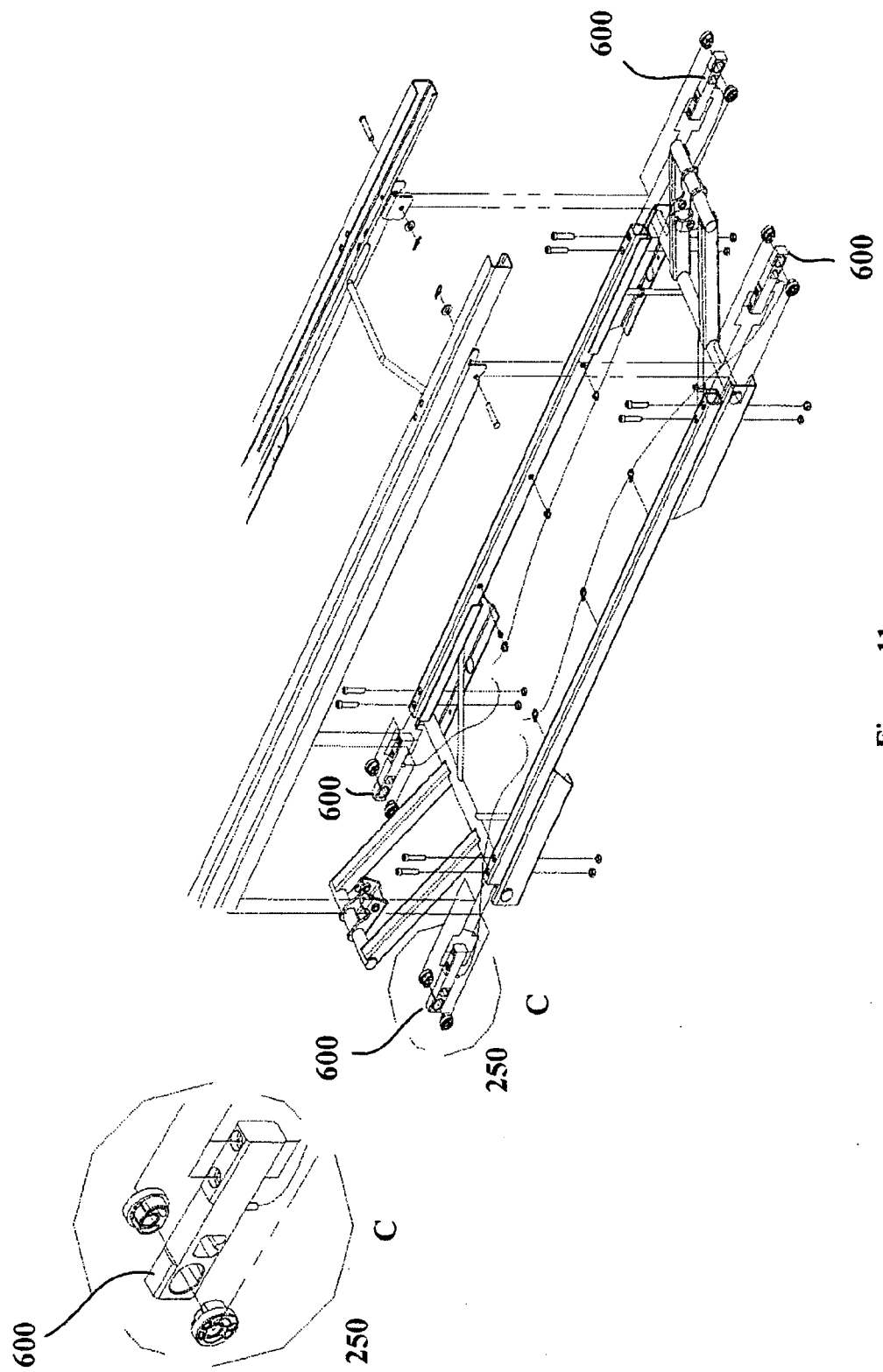
FIG. 11 is a perspective view depicting four load cells in relation to an intermediate frame according to one embodiment of the present invention.
Figure 12:
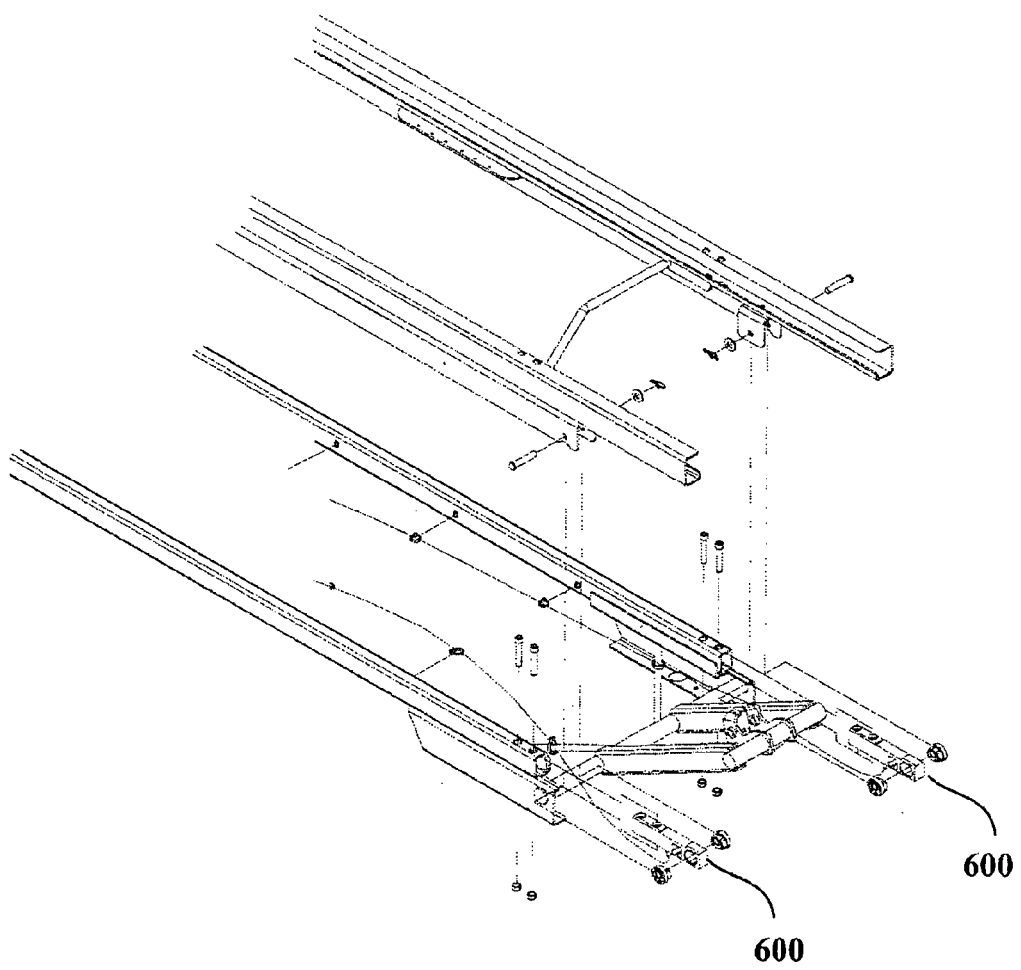
FIG. 12 is a partial perspective view of load cells in relation to a load frame and an intermediate frame according to one embodiment of the present invention.

FIG. 11 illustrates one embodiment of the present invention 600 are respectively located proximate to the four corners of the intermediate frame said intermediate frame being operatively connected to the load frame via the system of load cells 600. More specifically, the load cells 600 are coupled with the respective ends of the superior components of the intermediate frame and with complementary areas on the inferior components of the load frame. The superior components of the intermediate frame and the inferior components of the load frame are longitudinally adjacent but are not in contact, the sole physical connection between these components being through the load cells 600.

Figure 8:
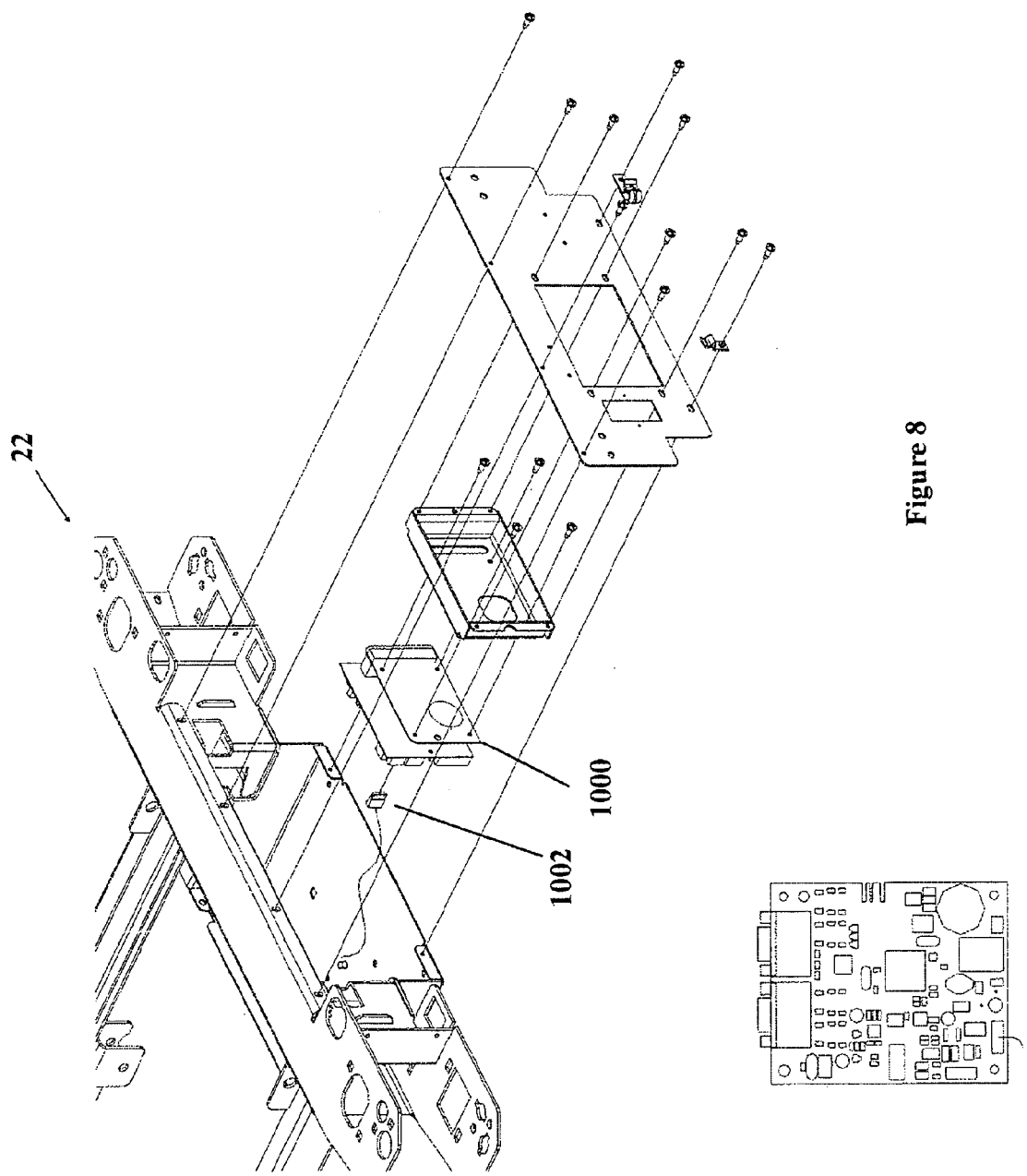
FIG. 8 depicts a top view of a tilt sensor circuit and its relative position to the head end casing of the load frame according to one embodiment of the present invention.
Figure 9:
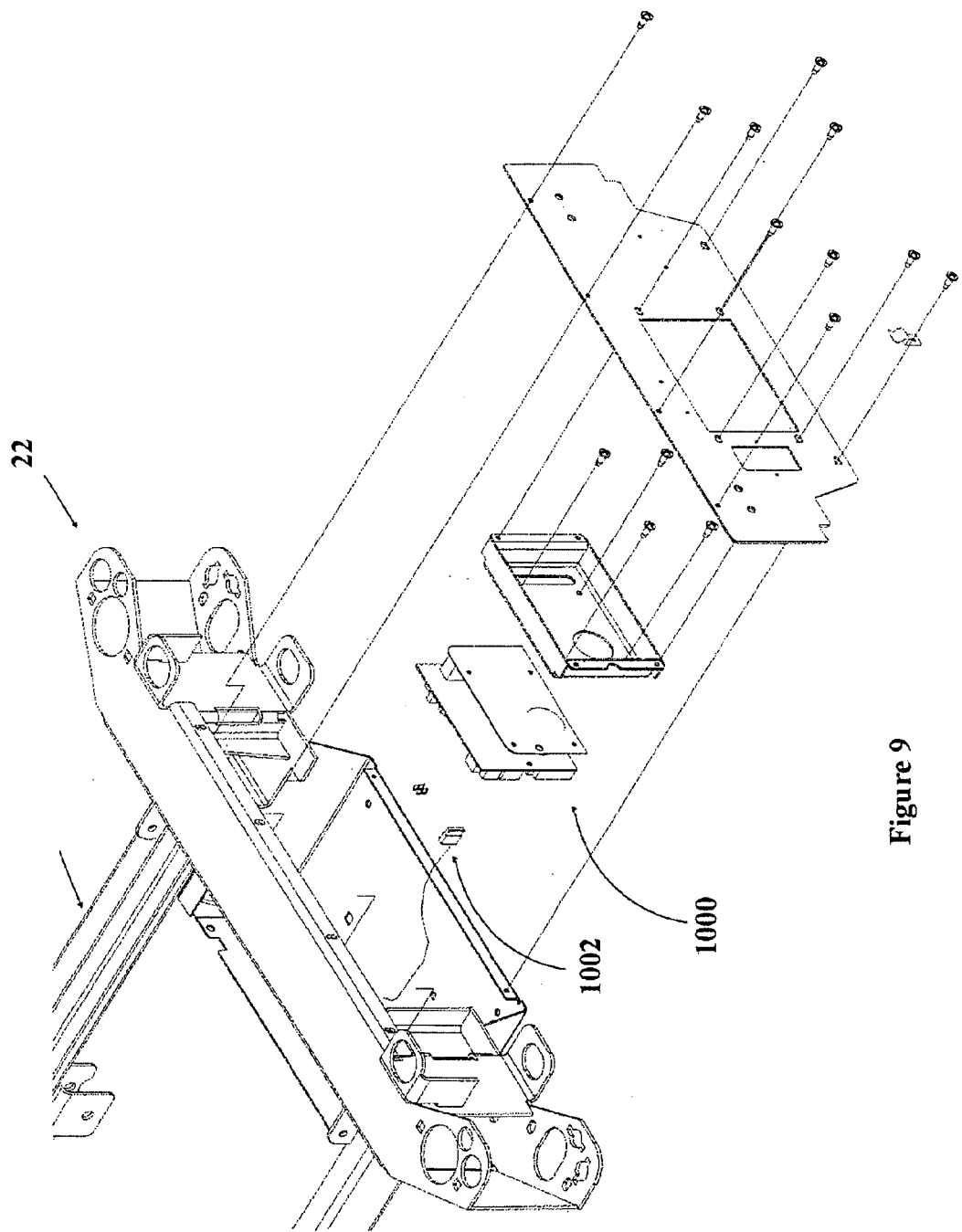
FIG. 9 depicts an exploded view of a tilt sensor circuit attached to the head end casing of the load frame according to one embodiment of the present invention.

In a patient support according to one embodiment of the present invention, the load cell 600 measurements can be used together with other measured or input information, such as the articulation angle of a section of the lying surface support or the entire load frame in order to determine, for example, a patient's weight. For example, when the patient support is angled to the Trendelenburg and reverse Trendelenburg positions, the actual load can be calculated by knowing the angle of the load frame and respective loads measured by each load cell, independent of the load frame's position. As depicted in FIGS. 8 and 9, one or more tilt sensors 1000 can determine the angular position of the load frame while the load's center of gravity shifts.

Medical personnel require accurate readings of the patient's weight independent of the patient support's articulation. Such a measurement is possible by calculating the patient support's angle relative to baseline and load cell 600 measurements.

A tilt sensor 1000, which incorporates an accelerometer, is attached to any part of the frame system that can be elevated, angled and/or articulated. FIG. 9 depicts an exploded view of an embodiment of a tilt sensor circuit 1000 attached to an end of the load frame.

The tilt sensor 1000 provides a signal that is read and measurements are calculated after a given time period, such as 50 ms. It can run continuously, intermittently or upon command from the user, such as when components of the frame system are in an articulated position. The tilt sensor 1000 is connected to at least one motherboard, processor or any electronic board via a communications network, fibre optic, or wireless connection 1002 to allow for a reading of the tilt sensor signal.

Figure 13:
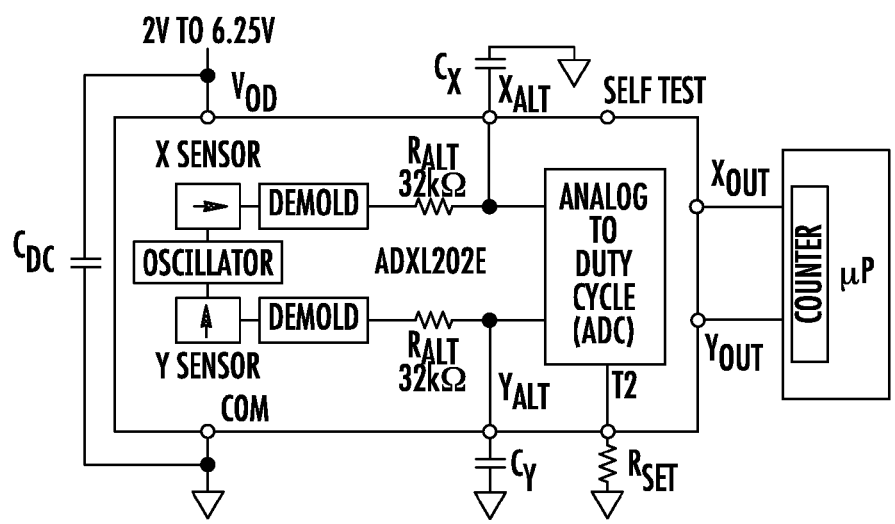
FIG. 13 depicts the functional block diagram of an accelerometer used in an embodiment of the present invention.
Figure 14:
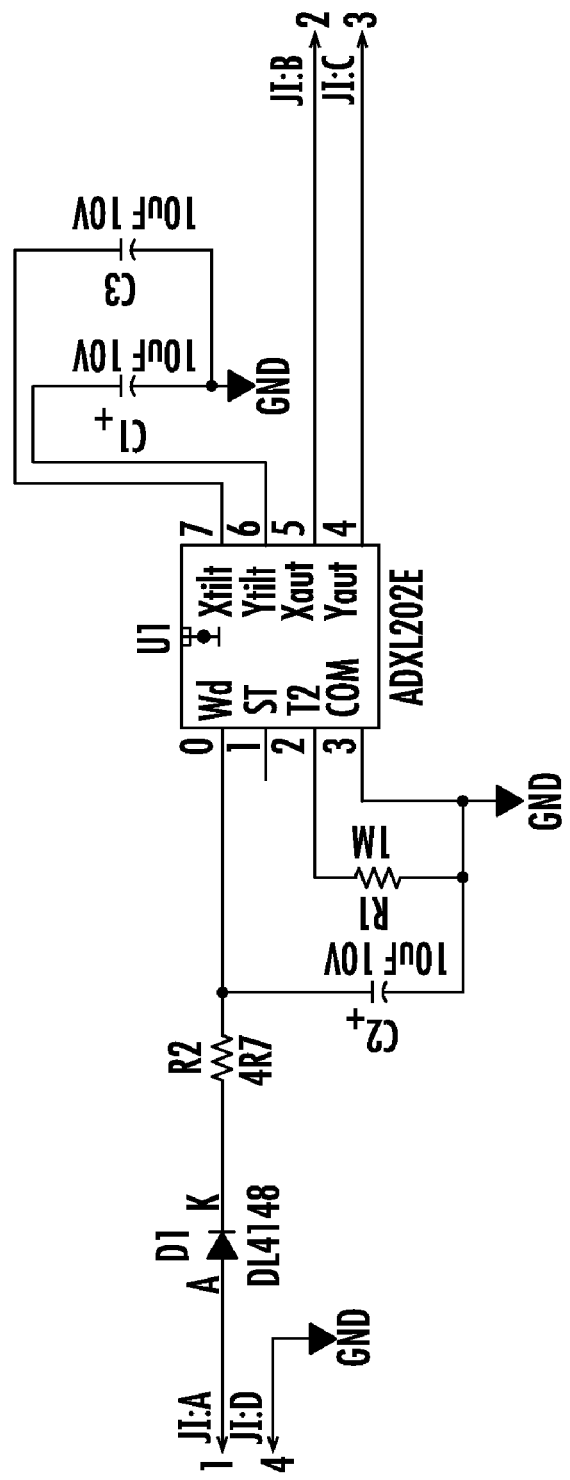
FIG. 14 displays a tilt sensor circuit according to an embodiment of the present invention.

In one embodiment, the tilt sensor 1000 is designed with a solid state accelerometer, such as the ADXL202E accelerometer from Analog Devices, Inc. of One Technology Way, Norwood, Mass.; schematically represented in FIGS. 13 and 14. Angular solid state sensors or electronic angular sensors, where a change in angle of the sensor changes the impedance of the sensor which can be measured, could also be used. Other accelerometers may also be used within the present invention, as would be understood by a worker skilled in the art to which this invention relates. The accelerometer of this embodiment is a 2 axis acceleration sensor with a direct interface to low-cost microcontrollers. This interface is possible through a duty cycle (ratio of the pulse width to the total period) output. The outputs of the accelerometer can be analog or digital signals whose duty cycles are proportional to acceleration. The outputs can be directly measured with an integrated microprocessor counter, without any external converter.

FIG. 13 depicts a functional block diagram of the accelerometer used in this embodiment. For each axis, a circuit output converts the signal into a modulated duty cycle that is decoded by the microprocessor. The accelerometer of this embodiment must be capable of measuring positive and negative accelerations to at least +−2 g, so as to measure static acceleration forces such as gravity and therefore be used in a tilt sensor 1000.

Theoretically, a 0 g acceleration produces a 50% nominal duty cycle. Acceleration is calculated as follows:

$$A(g)=(T1/T2-0.5)/12.5\%$$

$$T2(s)=R_{SET}(\Omega)/125\ M\Omega$$

The 12.5% corresponds to the theoretical gain of the accelerometer. When used as a tilt sensor 1000, the accelerometer uses the force of gravity as the input vector to determine the orientation of the object in space. The accelerometer is more sensitive to tilt when its reading axis is perpendicular to the force of gravity, that is to say, parallel to the earth's surface. When the accelerometer is orientated on axis to gravity, that is to say, near its +1 g or −1 g reading, the change in output acceleration per degree of tilt is negligible. When the accelerometer is perpendicular, the output varies nearly 17.5 mg per degree of tilt, but at 45 degrees the output only varies 12.2 mg by degree and the resolution declines. This is illustrated in the following table:

| X Axis Orientation to Horizon (°) | X Output (g) | X Output Δ per Degree of Tilt (mg) | Y Output (g) | Y Output (g) Δ per Degree of Tilt (mg) |
|---|---|---|---|---|
| −90 | −1.000 | −0.2 | 0.000 | 17.5 |
| −75 | −0.966 | 4.4 | 0.259 | 16.9 |
| −60 | −0.866 | 8.6 | 0.500 | 15.2 |
| −45 | −0.707 | 12.2 | 0.707 | 12.4 |
| −30 | −0.500 | 15.0 | 0.866 | 8.9 |
| −15 | −0.259 | 16.8 | 0.966 | 4.7 |
| 0 | 0.000 | 17.5 | 1.000 | 0.2 |
| 15 | 0.259 | 16.9 | 0.966 | −4.4 |
| 30 | 0.500 | 15.2 | 0.866 | −8.6 |
| 45 | 0.707 | 12.4 | 0.707 | −12.2 |
| 60 | 0.866 | 8.9 | 0.500 | −15.0 |
| 75 | 0.966 | 4.7 | 0.259 | −16.8 |
| 90 | 1.000 | 0.2 | 0.000 | −17.5 |

It is also to be noted that the gravity value varies according to the sine of the angle, which also influences the precision and consequently the orientation of the tilt sensor 1000 of this embodiment. The sensor precision can be improved by using both Xout and Yout signals in the angular determination. By doing so, the low sensitivity range (around 0 degrees) is reduced.

The tilt sensor circuit used in one embodiment was therefore designed from the Analog Devices Inc. accelerometer following the recommended design parameters. The schematic of the circuit for this embodiment is shown at FIG. 14.

D1 is added to protect the circuitry against polarity inversion.

$R_{SET}$ value was set to 1 MΩ. Therefore, T2 value is:

$$T2 = 1 \text{ M}\Omega / 125 \text{ M}\Omega = 0.008$$

T2 total period is thus 8 ms, therefore giving a 125 Hz frequency.

In order to determine the actual values of the zero and the gain, the tilt sensor circuit must be calibrated. Since the zero and the gain are known after calibration, only T1/T2 is unknown. It is this duty cycle that varies according to the angle: The microprocessor thus takes this reading and calculates the corresponding angle.

The tilt sensor 1000 circuit comprises an analog potentiometer which outputs a PWM (pulse width modulation) signal with a good signal-to-noise ratio. This PWM signal is sent to a microcontroller wherein the period of the signal is measured and the on-time of the signals. A ratio of these results is proportional to the sine of the angle. By using the cosine of this angle within a formula (discussed below) the precise angle can be determined. This analysis can be accomplished by a microprocessor.

To calibrate the tilt sensor circuit, two duty cycle readings must be taken at known angles.

With these two PWM readings, the two unknowns (zero and gain) can be computed. It is preferable to take a PWM reading when the tilt sensor is at its zero position, as readings are usually precise at this position. This also provides a reading of the PWM value corresponding to the zero of the tilt sensor, since a sensor in zero position gives 0 g.

The tilt sensors of this embodiment are used to indicate the angle of the load frame, such as the Trendelenburg and reverse Trendelenburg angles. A compensation of the weight read by the load cells according to the Trendelenburg angle can then be computed. Consequently, the weight value displayed is thus in the required margin.

As previously indicated, the axis in which the tilt sensor 1000 is positioned is important to obtain precise readings. For example, the position of a head section of the lying surface support may vary between 0 and 80 degrees. Given that the tilt sensor 1000 of the embodiment is more precise from −45 to 45 degrees than from 0 to 90 degrees, the tilt sensor would be positioned in the bed so that the zero of the sensor is at 45 degrees. In computation, one would account for this position by adding 45 degrees to each angle read.

Figure 15:
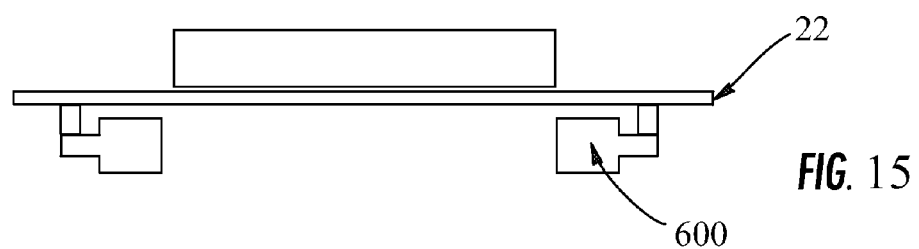
FIG. 15 depicts a horizontal patient support with a load according to an embodiment of the present invention.
Figure 16:
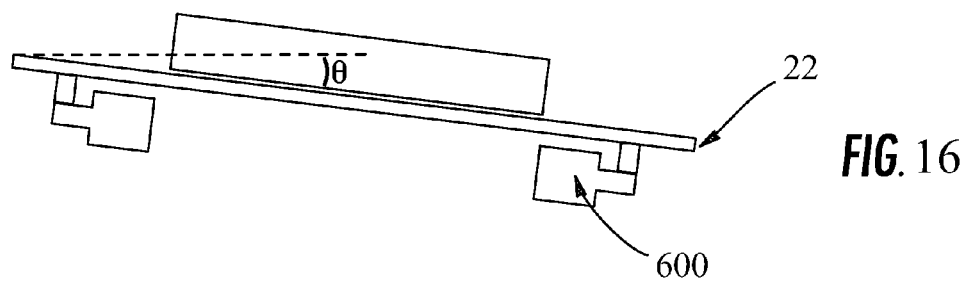
FIG. 16 depicts an inclined patient support with a load at angle θ according to an embodiment of the present invention.

The calculation of load and calibration values is readily apparent in referring to FIGS. 15 and 16, where:

X patient load;

$Y_+$ weight of patient support frame 22 which changes with the Trendelenburg angle;

$Z_+$ load cell 600 factor which is not influenced by the Trendelenburg angle;

$Y_-$ weight of bed frame 22 which changes with the reverse Trendelenburg angle;

$Z_-$ load cell 600 factor which is not influenced by the reverse Trendelenburg angle;

θ bed frame 22 angle; and

T load cell 600 readings.

$$A(t)\theta = 0°, T_0° = X + Y_+ + Z_+$$

$$At \theta = 12°, T_{12°} = (X_+ + Y_+)\cos\theta + Z+$$

During calibration, the load frame without the patient is measured at 0° and at 12°, providing:

$$X = 0$$

$T_{0°}$ = first measurement at 0°

$T_{12°}$ = second measurement at 12°

$$T_{0°} = Y_+ + Z_+$$

$$T_{12°} = Y_+ \cos\theta + Z_+$$

$$Y_+ = T_{0°} - Z_+$$

$$Y_+ \cos\theta = T_{12°} - Z_+$$

$$Y_+ = \frac{T_{12°} - Z_+}{\cos\theta}$$

$$T_{0°} - Z_+ = \frac{T_{12°} - Z_+}{\cos\theta}$$

$$Z_+ = \frac{T_{12°} - T_{0°}\cos\theta}{1 - \cos\theta}$$

if $e = 12°$ $$Z_+ = \frac{T_{12°} - T_{0°}\cos 12°}{1 - \cos 12°}$$

$$Z_+ = (T_{12°} - T_{0°} * 0.97815) * 45.761565$$

$$Y_+ = T_{0°} - Z_+$$

$Z_+$ and $Y_+$ for each load cell 600 are determined during calibration. In a similar manner, $Z_-$ and $Y_-$ are determined using measurements at 0° and −12°, providing:

$$Z_- = (T_{-12°} - T_0 0 * 0.97815) * 45.761565$$

$$Y_- = T_0° - Z_-$$

When determining the patient's weight, X, the following calculations are made for each load cell 600:

$$T_e = (X + Y)\cos 8 + Z$$

$$T_e = X\cos e + Y\cos e + Z$$

$$X\cos e = T_e - Y\cos e - Z$$

$$X = \frac{T_e - Y\cos e - Z}{\cos e}$$

$$X = \frac{T_e - Z}{\cos e}$$

The processor determines the load frame's angular position (Trendelenburg or reverse Trendelenburg) prior to choosing $Y_+$ or $Y_-$ and $Z_+$ or $Z_-$. When the load frame's angle is 0°, the processor chooses $Y_+$ and $Z_+$ to calculate the load.

The center of gravity can be calculated as follows, using for example four load cells 600 (schematically represented in FIG. 6) positioned in a rectangle relative to the patient:

X length (head to foot)

Y width (left to right)

LC(0) load cell value foot left

LC(1) load cell value head right

LC(2) load cell value foot right

LC(3) load cell value head left

W total weight of the patient

H(X) distance between the head load cells and foot load cells

H(Y) distance between the right load cells and left load cells $$CG[X] = \frac{LC(3) + LC(1)}{100} * H(X) * 0.01$$

$$CG[Y] = \frac{LC(3) + LC(0)}{\frac{W}{100}} * H(Y) * 0.01$$

This embodiment of a load cell system 600 can be used for monitoring movement of a patient. The system can be integrated into the patient support or can be part of a lying surface such as a mattress. In addition, the load cell system 600 can comprise a number of 10 load cells 600 or load sensors, for example a load cell 600 which can be embedded in the patient support proximally positioned at each of a supported person's limbs and optionally at the center of the patient support. The load cell system 600 also can be comprised of a mesh of load cells 600 for example. The signals from the load cells 600 can be monitored and processed by a processing unit in the load cell system 600 or a central processing unit 15 capable of monitoring, processing, and controlling signals from the patient support's various subsystems. Instead of forming part of a lying surface such as a mattress the load cell system 600 can also integrated into the lying surface support. The load cell system 600 can provide a measure for the pressure, weight, or mass load of a certain load cell 600, for example foot left or right load cell values and head left or right load cell values and additional information about the location of the center of gravity.

In one embodiment of the present invention, the tilt sensors 1000 can provide a means for determining possible interference between components of the patient support. For example, if a particular component is in a certain relative position, a second component might not be able to perform certain functions associated with it. In this embodiment, there can furthermore be a movement termination based on the evaluation of tilt sensors 1000 readings.

In a further embodiment of the present invention, tilt sensors 1000 can be used to evaluate a patient's position over a period of time through the collection of angle variation data.

In one embodiment, a collection of angular data from the tilt sensors 1000 can also provide assistance for the maintenance of the patient support. For example it can help to determine the angle of a particular patient support component and the period of time that that position is held, especially when a particular position results in higher stress levels being applied to specific components of the patient support.

In an another embodiment of the present invention, tilt sensors 1000 can be positioned on the elevation system for determination of the height of the patient support surface.

In an another embodiment of the present invention, tilt sensors 1000 are wireless. In a further embodiment, tilt sensors 1000 do not have an on board power supply and are powered in the same way as for example an RFID tag, by the scanning frequencies sent by a scanner for example. In another embodiment, tilt sensors are integrated within load cells 600.

A worker skilled in the art would understand that tilt sensors 1000 could be positioned in a plurality of other components of the patient support, for example, the siderails, a control panel, on an intravenous apparatus support attached to a patient support, etc.

In one embodiment the control and diagnostic system can comprise an additional scale subsystem providing a calibration process for calibrating the scale subsystem to provide accurate reading of a patient's weight and subsequently to calibrate a motion detection system for monitoring movement of the patient. It may be necessary to calibrate the load cells electronics in order to provide match the sensor signals with the scale subsystem electronics.

In one embodiment, the tilt sensors 1000 can be used with a control and diagnostic system as a means for fault detection. For example, where no change in an angle is detected when an actuator is being activated to modify said angle, the situation can be indicative of a blockage related to the actuator movement or an actuator malfunction.

FIG. 6 illustrates the information made available by a load cell system 600, which is used for monitoring movement of a patient. The system can be integrated into the patient support or can be part of a person support element such as a lying surface. In addition, the load cell system can comprise a number of load cells 600 or load sensors for example a load cell 600 which can be embedded in the patient support proximally positioned at each of a supported person's limbs and optionally at the center of the patient support. The load cell system 600 also can be comprised of a mesh of load cells for example. The signals from the load cells can be monitored and processed by a processing unit in the load cell system 600 or a central processing unit capable of monitoring, processing, and controlling signals from the patient support's subsystems. Instead of forming part of a support element, the load cell system can be integrated into the surface of the patient support frame. The load cell 600 system can provide a measure for the pressure, weight, or mass load of a certain load cell 600, for example foot left or right load cell values and head left or right load cell values and additional information about the location of the centre of gravity.

Figure 17:
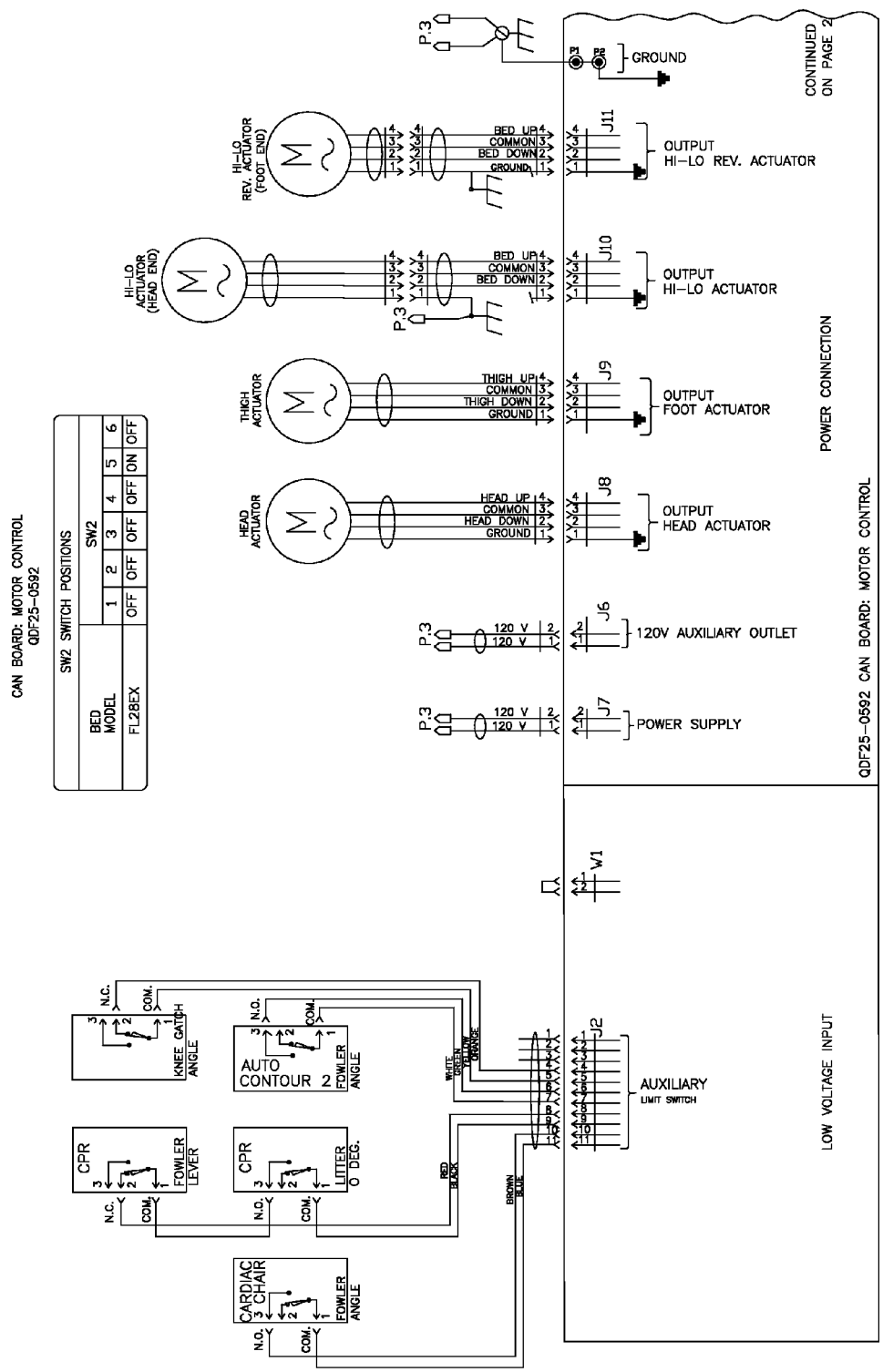
FIG. 17 illustrates a motor control and drive system according to one embodiment of the present invention.

FIG. 17 schematically illustrates an embodiment of the motor control subsystem with a number of attached actuators and limit switches. It is understood that, depending on the functionality of the patient support, there can be a different number of actuators or limit switches than illustrated. In this embodiment the surface of the patient support can be shaped by orienting a head, thigh, and a foot section where the support surface for a supported person is intended to fold and provide an adjustable angle between the upper body and the thigh as well as under the knee between the thigh and the lower leg. The head actuator can position the end of the head section, and the thigh actuator can position the knee section of the patient support surface relative to an even or flat support structure. The HI-LO head actuator can position the head end of the even support structure relative to the frame of the patient support which is in contact with the floor. The HI-LO foot actuator can position the foot end of the even support structure relative to the frame of the patient support, for example. The two HI-LO actuators can pivot the support surface horizontally whereas the head and the thigh actuator can shape the support surface by pivotally adjusting sections of the patient support surface.

The motor control subsystem is connected to a number of limit switch or angle sensor systems which ensures that the actuators do not move or position parts beyond predetermined limit angles or distances. When a part or section of the patient support reaches a predetermined limit position while moving, the motor control subsystem can receive a status change signal via one or more limit sensor signals and can interrupt the respective movement. The motor control subsystem can have a safety control feature that does not allow any further continued movement in that same direction or orientation unless the limit condition indicated by the limit sensor system is resolved. Provided that no movement of other degrees of freedom of the patient support takes place, the limit condition typically can be resolved by reversing the original movement.

Figure 18:
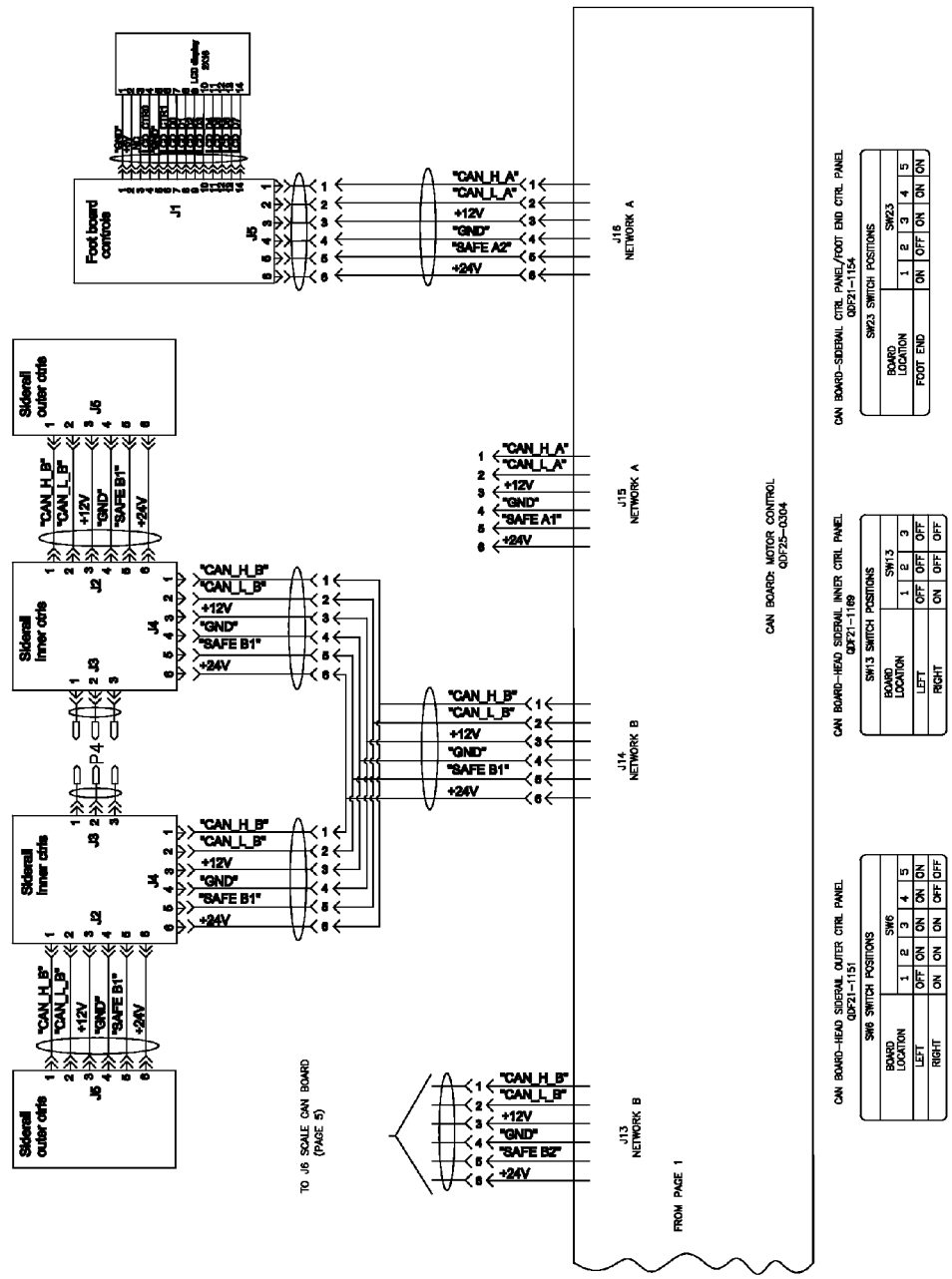
FIG. 18 illustrates an interface controller according to one embodiment of the present invention.

FIG. 18 schematically illustrates an embodiment of the user interface controller with a number of attached user interface consoles. The patient support can have a number of user interface consoles, each providing access to a certain set of patient support system functions. For example the patient support can have user interface consoles integrated into one or both of the side rails of the patient support providing easy access to certain patient support system functions for a supported person or for a person at the side of the patient support. The patient support can also have a user interface console located at the foot or the head section of the patient support. Each such interface console may be integrated into a respective foot or head board of the patient support for example. A foot or a head interface console may provide access to a set of patient support system functions different from each other as well as different from the side rail consoles. There can be inner or outer side rail consoles intended for access from within or from outside of the patient support. The foot board console can have a display system included. The display system can be a touch screen display or a simple passive display system with a separate input system. In addition the interface controller can have a remote control interface to which a remote console can be connected. The remote control interface can provide wired or wireless connection of a special purpose or a general purpose computing device for example. A number of different bus systems and control protocols are available to communicate through the remote control interface as known to a person skilled in the art. The interface controller may also provide a number of additional control or remote control interfaces.

Figure 19:
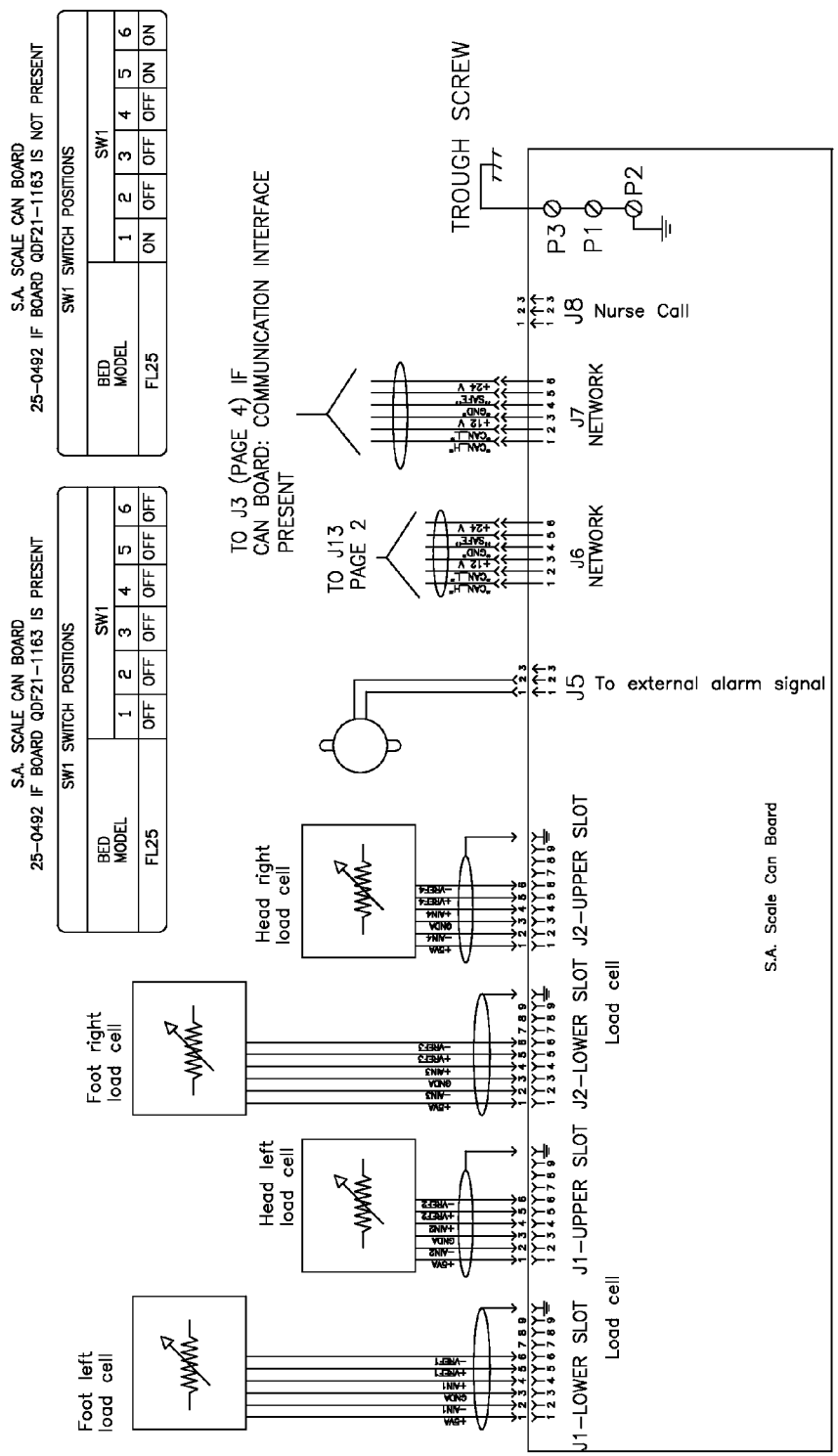
FIG. 19 illustrates a scale subsystem according to one embodiment of the present invention.

FIG. 19 illustrates a part of a scale subsystem. The scale subsystem can connect to a number of load sensors or load cells. The number of load sensors can be different from that illustrated. In this embodiment, four load sensors which are capable of sensing pressure and can be calibrated to provide a measure of force or mass applied to each sensor are attached to the scale subsystem control interface. The scale subsystem controller can process signals incoming from the load cells and can be used to detect the status of a supported person. The scale control subsystem can be configured to provide a messaging signal or to alert monitoring personnel through an external alarm system interface for example. When each load cell is properly calibrated, the scale control subsystem can also provide a measure of the weight of a supported person, which is then compensated by the angle of the patient support to provide the actual weight. The weight information can be utilized and can also be recorded in another subsystem of the patient support which may be desired for patient monitoring for example. As previously described, the angle of the patient support and the load sensor measurements are used to calculate the patient's actual weight, independent of the patient support's position.

Figure 20:
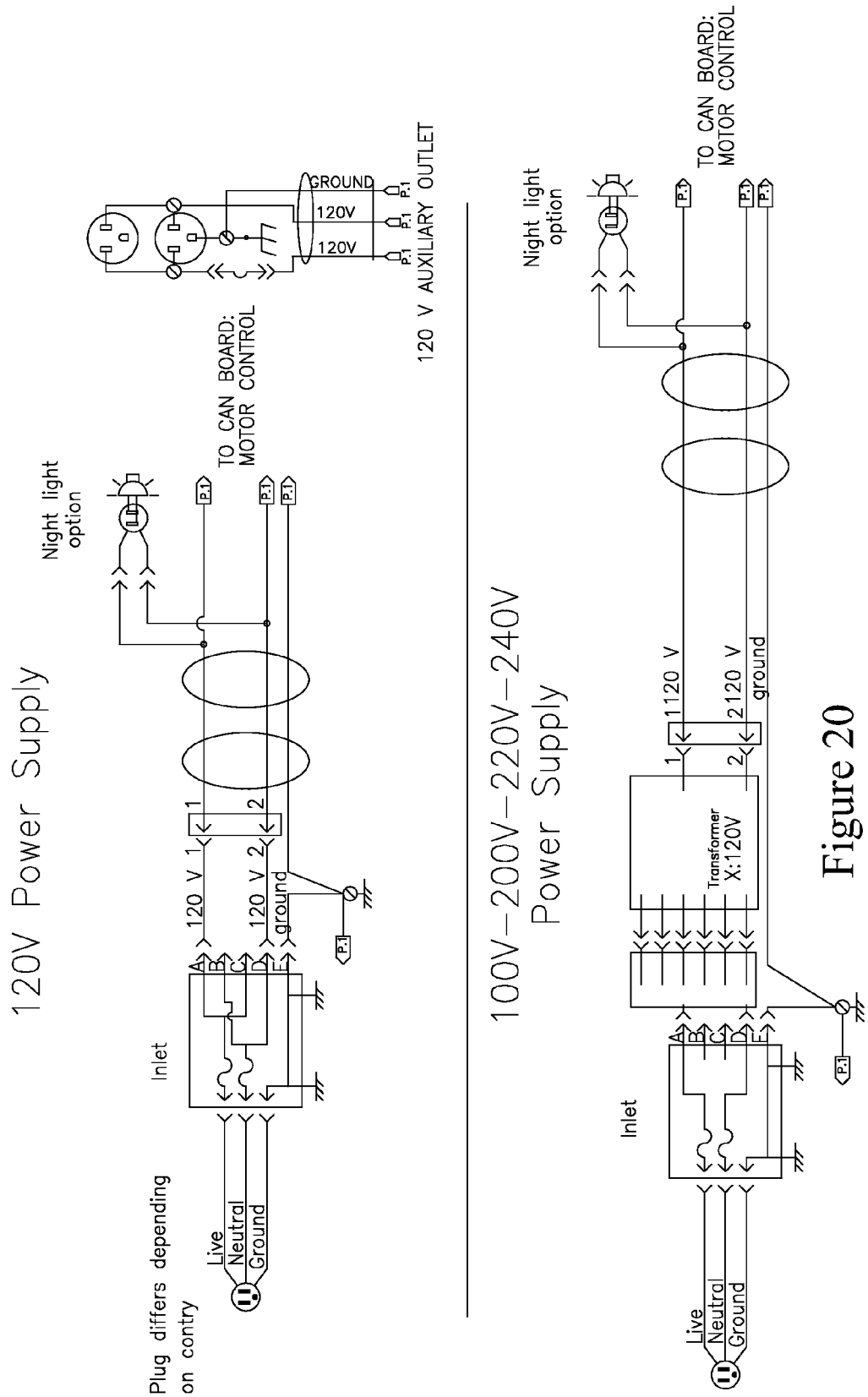
FIG. 20 illustrates a power supply system according to one embodiment of the present invention.

FIG. 20 illustrates an embodiment of a power supply system. The power supply system may include an adaptation subsystem including a transformer and an adaptive wiring and plugging subsystem to achieve compatibility with standard power outlets and the different voltage standards of other regions or countries.

Figure 21:
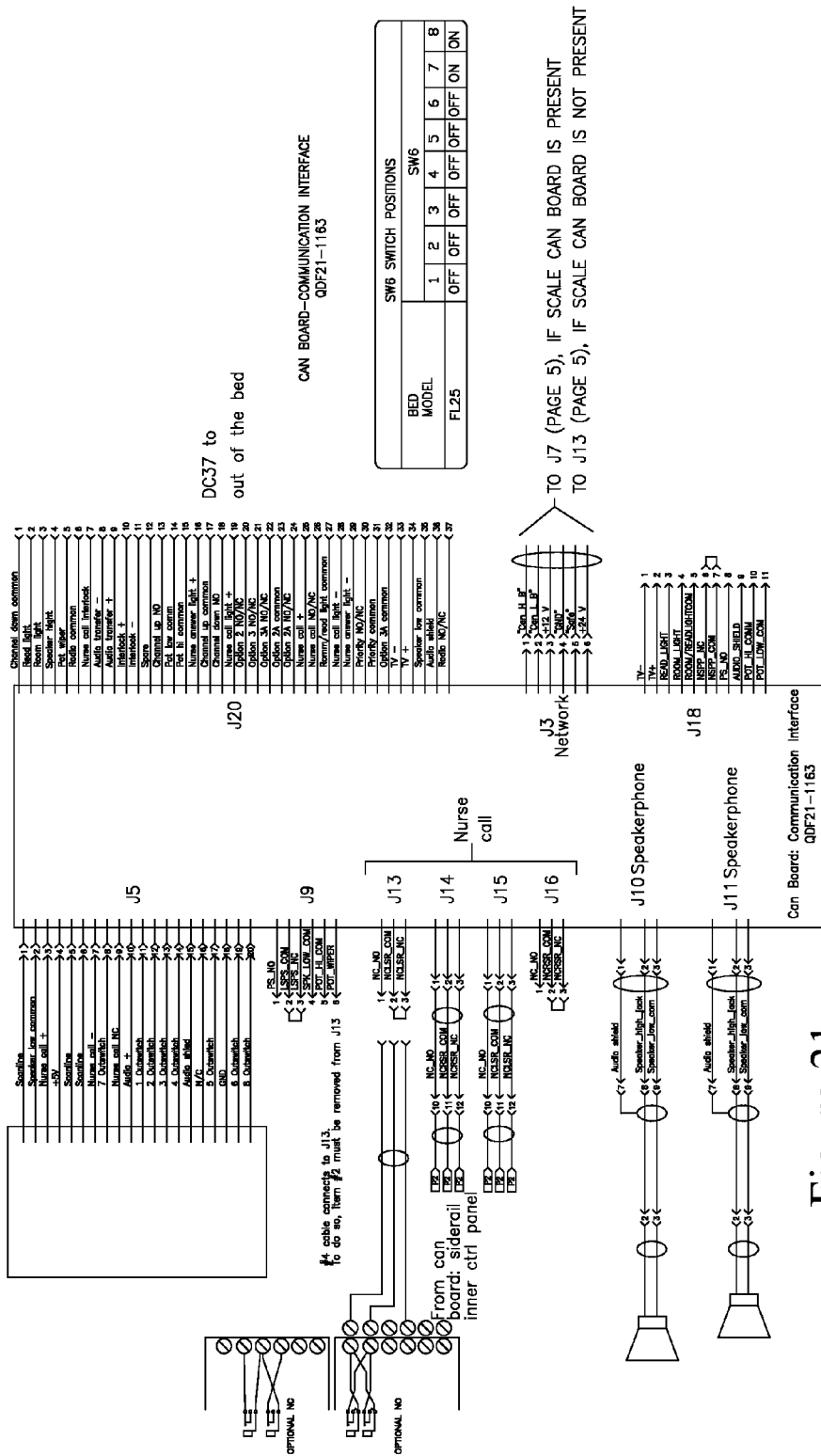
FIG. 21 illustrates a communication interface according to one embodiment of the present invention.

FIG. 21 schematically illustrates the communication interface of the CAN board controller for communication with other components of the patient support. The communications interface includes subinterfaces for side rail consoles, footboard consoles, remote monitoring consoles, external alarm system, speakers, an entertainment system etc.

Patient Support System Components

A multifunctional patient support can be equipped with one or more of a plurality of electronic devices that can provide a means for controlling the functionality of the patient support. For example, electronically controlled drivers or actuators can be provided to help automatically adjust any part or section of a patient support, wherein these actuators can be electrical, pneumatic or hydraulic in nature and may require a suitable electrical, pneumatic or hydraulic drive or power supply system for operation thereof. A patient support system can additionally include one or more sensors and detectors for sensing and detecting the status of structural or functional components of the patient support as well as certain vital signs of a patient. For example, sensors or detectors can be appropriately designed load sensors, angular movement sensors, pressure sensors, temperature sensors or any other type of sensor or detector that would be appropriate for integration into a patient support as would be readily understood by a worker skilled in the art. Each of these sensors or detectors can be configured to evaluate a desired piece of information relating to the supported person or the patient support itself, for example the information can relate to the mass of the patient, the orientation of the patient support in terms of position of the supported person or other characteristics.

In addition, the patient support system comprises a form of human-machine interface system that can assist in accessing the functionalities that are associated with the patient support, for example to enable movement of portions of the patient support or to evaluate the condition of desired aspects of the patient support's functionality, such as monitoring or fault detection, for example. The interface system can be realised with one or more specific interfaces for enabling access, wherein interfaces can be provided on a footboard, headboard, side rails or other locations on the patient support for example. The position and number of interfaces can be determined based on the number of desired access points to the various functionalities of the components of the patient support.

In one embodiment, the patient support system components further comprises a sensor for detecting if a patient is inadvertently obstructing the selected movement of the patient support. For example, if a patients arm is below a side rail, a sensor can detect the presence of the arm and not proceed with the lowering of the side rail if this request has been made. In this manner, the diagnostic and control system can monitor and evaluate if a patient's orientation or position would inhibit a selected movement of patient support component.

It is obvious that the foregoing embodiments of the invention are exemplary and can be varied in many ways. Such present or future variations are not to be regarded as a departure from the spirit and scope of the invention, and all such modifications, as would be obvious in the art, are intended to be included within the scope of the following claims.

The embodiments of the invention in which an exclusive property or privilege is claimed are defined as follows:

1. A control system for a patient support, said patient support having integrated therein one or more electronically controlled devices for moving a component of the patient support, said system comprising:
   a) an actuator subsystem electronically coupled to the one or more electronically controlled devices for controlling the functionality of the one or more electronically controlled devices,
   b) a data logger electronically coupled to the one or more electronically controlled devices, said data logger counting the movement of the component of the patient support and storing the counted movement in a data log; and c) a user interface electronically coupled to the actuator subsystem and the data logger, said user interface allowing a user to access said data log.

2. The system as described in claim 1 wherein the data log further comprises information from other subsystems of the patient support.

3. The system as described in claim 2 wherein the information in the data log is further categorized according to predetermined schemes.

4. The system as described in claim 3 wherein the information in the data log is in one or more formats chosen from a list comprising encoded, encrypted or clear text messages.

5. The system as described in claim 4 wherein each subsystem has its own logging mechanism for logging events specific to that subsystem and wherein the information in the data log is accessible only through an interface of the subsystem.

6. The system as described in claim 1 wherein the data log is located in an embedded controller.

7. The system as described in claim 1 wherein the data log records are located in a remote controller.

8. The system of claim 1 wherein said actuator subsystem includes a motor for raising a head portion of the patient support.

9. The system of claim 1 wherein said actuator subsystem includes a motor for raising a foot portion of the patient support.

10. The system of claim 1 wherein said actuator subsystem includes a motor for raising a thigh section of the patient support.

11. The system of claim 1 wherein said data logger encrypts the data in the data log.

* * * * *

UNITED STATES PATENT AND TRADEMARK OFFICE
CERTIFICATE OF CORRECTION

PATENT NO. : 7,702,481 B2
APPLICATION NO. : 11/362365
DATED : April 20, 2010
INVENTOR(S) : Jean-Paul Dionne et al.

It is certified that error appears in the above-identified patent and that said Letters Patent is hereby corrected as shown below:

Column 4
Line 57, insert --25-- after "24,"

Column 9
Line 37, "tog" should be --log--

Column 14
Line 5, "light" should be --right--

Column 16
Line 18, insert --Sensors to-- after "Tilt"

Column 21
Line 5, the equations should be $$CG[X] = \frac{LC(3)+LC(1)}{\frac{W}{100}} * H(X) * 0.01 \qquad CG[Y] = \frac{LC(3)+LC(0)}{\frac{W}{100}} * H(Y) * 0.01$$

-- --

Signed and Sealed this
Thirty-first Day of May, 2011

David J. Kappos
*Director of the United States Patent and Trademark Office*